United States Patent
Shetty

(10) Patent No.: US 11,433,111 B2
(45) Date of Patent: Sep. 6, 2022

(54) COMPOSITION FOR TREATMENT AND MANAGEMENT OF DEMENTIA AND COGNITIVE DYSFUNCTION AND METHOD OF PREPARATION THEREOF

(71) Applicant: Muniyal Ayurvedic Research Centre, Manipal (IN)

(72) Inventor: M Vijayabhanu Shetty, Karnataka (IN)

(73) Assignee: Muniyal Ayurvedic Research Centre, Manipal (IN)

( * ) Notice: Subject to any disclaimer, the term of this patent is extended or adjusted under 35 U.S.C. 154(b) by 226 days.

(21) Appl. No.: 16/808,726

(22) Filed: Mar. 4, 2020

(65) Prior Publication Data

US 2020/0197474 A1    Jun. 25, 2020

Related U.S. Application Data

(60) Provisional application No. 62/814,528, filed on Mar. 6, 2019.

(51) Int. Cl.

| | | |
|---|---|---|
| *A61K 36/81* | (2006.01) | |
| *A61K 47/36* | (2006.01) | |
| *A61P 25/28* | (2006.01) | |
| *A61K 36/68* | (2006.01) | |
| *A61K 36/39* | (2006.01) | |
| *A61K 36/48* | (2006.01) | |
| *A61K 35/02* | (2015.01) | |
| *A61K 36/24* | (2006.01) | |
| *A61K 45/06* | (2006.01) | |
| *A61K 36/882* | (2006.01) | |
| *A61K 36/185* | (2006.01) | |
| *A61K 35/04* | (2006.01) | |
| *A61K 36/35* | (2006.01) | |

(52) U.S. Cl.
CPC ............ *A61K 36/81* (2013.01); *A61K 35/02* (2013.01); *A61K 35/04* (2013.01); *A61K 36/185* (2013.01); *A61K 36/24* (2013.01); *A61K 36/35* (2013.01); *A61K 36/39* (2013.01); *A61K 36/48* (2013.01); *A61K 36/68* (2013.01); *A61K 36/882* (2013.01); *A61K 45/06* (2013.01); *A61K 47/36* (2013.01); *A61P 25/28* (2018.01)

(58) Field of Classification Search
None
See application file for complete search history.

(56) References Cited

PUBLICATIONS

Verma, S., et al., Study of Convolvulus pluricaulis for antioxidant and anticonvulsant activity, Cent Nerv Syst Agents Med Chem Mar. 2012;12(1):55-9, Abstract only.*
Gupta, J., et al., Isolation and Extraction of Flavonoid from the Leaves of *Rauwolfia serpentina* and Evaluation of DPPH-scavenging Antioxidant Potential, Oriental Journal Of Chemistry, 2015, vol. 31, (Spl Edn): Month : Oct. p. 231-235.*
Vollala, V.R., et al., Effect of Bacopa monniera Linn, (brahmi) extract on learning and memory in rats: A behavioral study, Journal of Veterinary Behavior, vol. 5, Issue 2, Mar.-Apr. 2010, pp. 69-74.*
Kanyal, N., Role of Rauwolfia serpentina in stroke induced experimental dementia, Indian J. Pharm. Biol. Res. 2016; 4(1):19-30, Abstract only attached.*
Pujari, G.R.S., et al., Effects of *Celastrus paniculatus* Willd. and *Sida cordifolia* Linn. in Kainic Acid Induced Hippocampus Damage in Rats, Indian Journal of Pharmaceutical Education and Research | vol. 53 | Issue 3 | Jul.-Sep. 2019.*
Bredesen, D.E., Rao, R.V., Ayurvedic Profiling of Alzheimer's Disease, Alternative Therapies, May/Jun. 2017 vol. 23 No. 3, 46-50.*
Kulkarni, R. et al., Rasayana Herbs of *Ayurveda* to Treat age Related Cognitive Decline: An Update, Pharmacogn. J. 2016;8(5):411-423.*

* cited by examiner

*Primary Examiner* — H. Sarah Park
(74) *Attorney, Agent, or Firm* — Pilloff Passing & Cosenza LLP; Sean A. Passino; Rachel K. Pilloff

(57) ABSTRACT

The invention relates to a composition for treatment and management of Dementia. The composition is a combination of herbs and bhasmas. It includes herbs such as Bacopa monnieri, Convolvulus pluricaulis, Mucuna pruriens, Nardostachys jatamansi, Rauwolfia serpentina, Withania somnifera, Acorus calamus, Sida cordifolia and Emblica officinalis. It further includes Shilajit, Rasa sindura and bhasmas. The composition is useful in treating Cognitive dysfunction, Dementia and other cognitive impairments associated with neuro-degenerative disorders. Further, the composition is also useful in restoring and improving cognitive function.

19 Claims, 5 Drawing Sheets

COMPOSITION FOR TREATMENT AND MANAGEMENT OF DEMENTIA AND COGNITIVE DYSFUNCTION AND METHOD OF PREPARATION THEREOF

CROSS REFERENCE TO RELATED APPLICATION

This application is based on and claims the benefit of U.S. Provisional Application 62/814,528 filed on 6 Mar. 2019, the contents of which are incorporated herein by reference in their entirety.

TECHNICAL FIELD

The embodiments disclosed in this specification relate to herbal compositions in the treatment and management of Cognitive dysfunction and more particularly in the treatment of dementia arising from neurodegenerative diseases. It also relates to the process of preparation of such composition.

BACKGROUND

Neuro-degenerative conditions are caused by progressive degeneration of central and peripheral nervous system. This degeneration of the nervous system may be due to progressive damage or death of neurons. Parkinson's disease and Alzheimer's disease are the most common neuro-degenerative disorders. Usually considered a disease of old age, these conditions affect a person's thinking and reasoning capabilities. The impairment in cognitive function is the most debilitating effect of neurodegenerative diseases. Further characteristics of neuro-degenerative disorders include tremors, gait impairment, olfactory impairment, psychiatric problems, sleep disorders, fatigue, etc.

Cognitive dysfunction is usually seen in all neurodegenerative diseases and is prominent in Alzheimer's disease. The progressive deterioration in cognitive function may ultimately lead to dementia. Dementia itself is not a disease but is a condition that may arise due to impairment in cognitive function. Dementia is a term generally used to describe loss or decline in a person's memory and other mental skills which poses a challenge in his/her day-to-day life. Dementia as such may be of various types depending on how it is caused such as Dementia due to Alzheimer's, vascular dementia, dementia due to Lewy bodies, etc. Alzheimer's associated dementia is the most common form of Dementia. Factors other than neuro-degenerative diseases may also lead to the development of dementia. Further, non-neurodegenerative conditions such as atherosclerosis may also, in some cases, result in Dementia. Plaque formation in arterial walls leading to interruptions in blood flow to brains cells is identified as Vascular dementia. In some cases, Alzheimer's and vascular dementia may occur at the same time leading to a condition of mixed dementia.

Clearly, various factors could affect one's cognitive functions which may further develop into Dementia. Leading a life with deteriorating thinking and reasoning capabilities can be challenging and stressful. In the initial stages the symptoms may be minimal. However, the symptoms may worsen at later stages leading to memory loss and impairment in motor functions. Such debilitating conditions could also lead to anxiety and depression.

While there are many therapeutic approaches to manage neuro-degenerative conditions and dementia, there is no single specific cure. The various methods of treatment currently being used involve medication that can delay the course of the disease and thus alleviate symptoms. Dopamine agonists, Cholinesterase inhibitors, Memantine etc. are commonly used to manage the neuro-degenerative manifestations. However, these allopathic interventions have been observed to have undesirable side effects and are inefficient.

Alternatively, ayurvedic interventions in management of Dementia and improvement of cognitive function are being considered by many as providing a safe and holistic approach of therapy. Various formulations having herbs such as *Convolvulus pluricaulis, Bacopa monnieri, Centella asiatica, Nardostachys jatamansi* and so on are popular and are being used as nervine tonics to improve cognitive function and memory. However, there exists a need for improved treatment methods that offer better and efficient healing and rejuvenation in patients having Dementia and cognitive dysfunction.

OBJECTS

The principal object of the embodiments disclosed herein is to provide a composition and method for treatment and management of cognitive dysfunction associated with neuro-degenerative diseases.

A second object of the embodiments disclosed herein is to provide a composition and method for the treatment and management of Dementia associated with neuro-degenerative diseases.

Another object of the embodiments disclosed herein is to provide a composition and method for the treatment and management of neuro-degenerative diseases.

A further object of the embodiments disclosed herein is to provide a composition and method for alleviating the symptoms associated with neuro-degenerative diseases.

Yet another object of the embodiments disclosed herein is to provide a composition and method for improving cognitive function in children.

A further object of the embodiments disclosed herein is to provide a composition and method for restoration/enhancement of memory in individuals.

Furthermore, an object of the embodiments disclosed herein is to provide an herbal composition and a method for its preparation.

These and other objects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF FIGURES

The embodiments disclosed herein are illustrated in the accompanying drawings, throughout which like reference letters indicate corresponding parts in the various figures. The embodiments herein will be better understood from the following description with reference to the drawings, in which.

DETAILED DESCRIPTION

Figure 1:
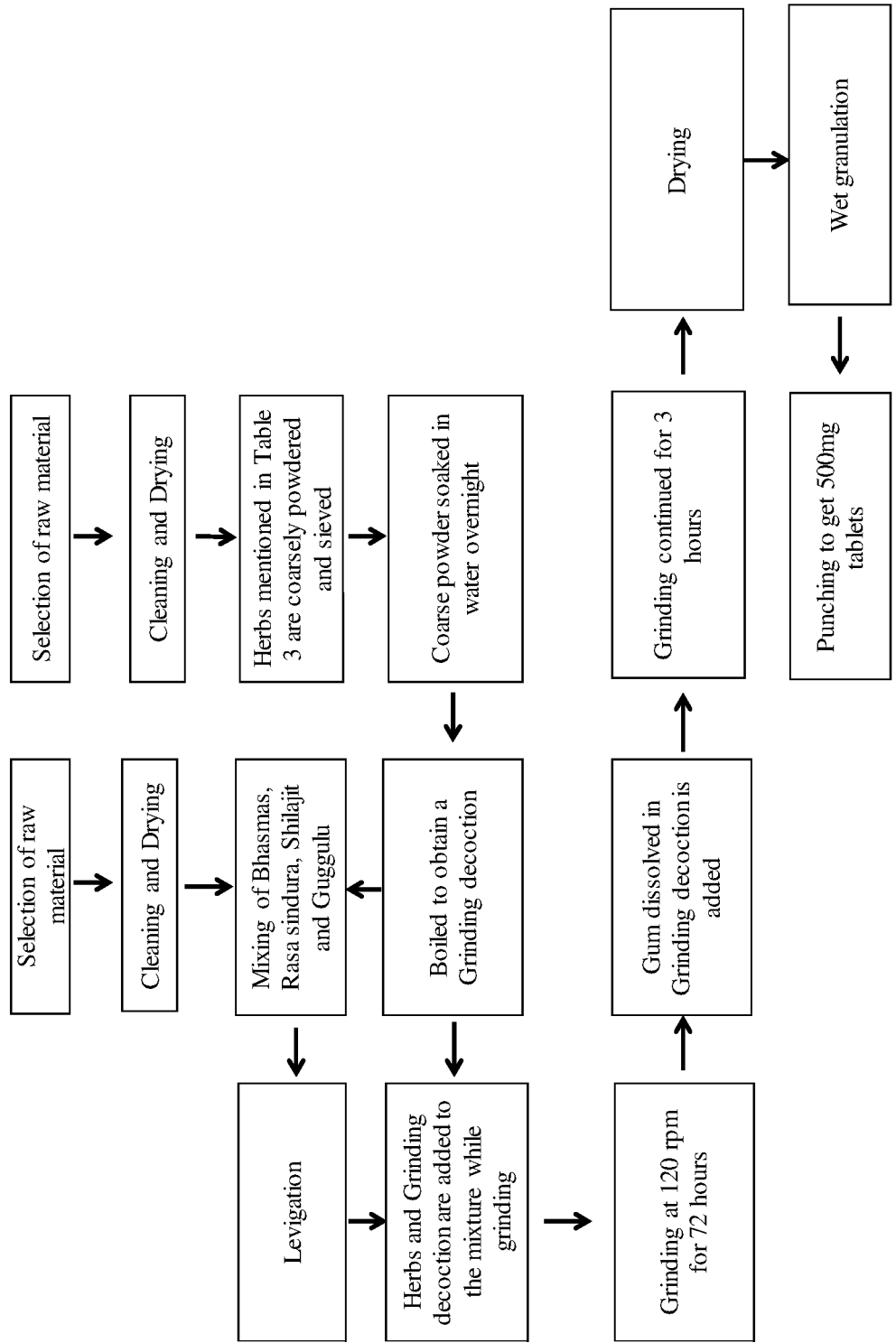
FIG. 1 depicts a flowchart for preparation of fortified tablets, according to embodiments as disclosed herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein achieve an herbal composition of therapeutic value, and a process for preparation of the composition. The herbal composition disclosed herein is useful in the treatment and management of Cognitive dysfunction. The embodiments of the disclosed composition are particularly useful in treatment and management of Dementia. The embodiments of the disclosed composition may be used to boost memory in children and adults. In various embodiments, the composition disclosed herein may be used to enhance or restore memory of an individual. Further, the disclosed composition is also instrumental in the treatment and management of neuro-degenerative diseases and associated symptoms. Accordingly, embodiments of a method for treatment and management of neuro-degenerative diseases and associated symptoms are also provided herein. The symptoms of neuro-degenerative diseases include the generally known symptoms such as apathy, anxiety, memory loss, speech changes, etc.

Composition

The disclosed embodiments herein provide herbal composition having a combination of selected herbs and minerals. In an embodiment, the herbal composition includes herbs and minerals. In another embodiment, the herbal composition includes herbs, minerals and at least one suitable excipient.

Herbs

In an embodiment, the composition comprises of *Bacopa monnieri, Convolvulus pluricaulis, Mucuna pruriens, Nardostachys jatamansi, Rauwolfia serpentina, Withania somnifera, Acorus calamus, Sida cordifolia,* and *Emblica officinalis,* or their extracts, or the active ingredients extracted from these herbs. In an embodiment, the composition further includes at least one of the following herbs: *Santalum album, Pterocarpus santalinus, Glycyrrhiza glabra, Terminalia chebula, Terminalia bellerica, Zingiber officinale, Piper nigrum, Piper longum, Curcuma longa, Inula racemosa, Cinnamomum zeylanica, Elettaria cardamomum, Syzygium aromaticum, Ocimum sanctum, Tinospora cordifolia, Hemidesmus indicus, Vetiveria zizanioides, Alpinia galangal, Cassia fistula, Embelia ribes, Prunus cerasoides, Rubia cordifolia, Ricinus communis, Boerhavia diffusa, Terminalia arjuna, Commiphora mukul, Picrorhiza kurroa, Plumbago zeylanica* and *Mesua ferrea,* or their extracts, or the active ingredients extracted from these herbs.

The composition includes a specific part of the herb (referred to herein as "herb component") such as roots, flowers, fruits, stem, bark, resin, rhizome, whole plant, extract etc. In an embodiment, the composition includes whole plant of *Bacopa monnieri* and *Convolvulus pluricaulis*; seeds of *Mucuna pruriens*; rhizome of *Nardostachys jatamansi*; roots of *Rauwolfia serpentina, Sida cordifolia, Withania somnifera* and *Acorus calamus*; and fruits of *Emblica officinalis*. In another embodiment, the composition further includes roots of *Picrorhiza kurroa, Plumbago zeylanica, Rubia cordifolia, Hemidesmus indicus, Vetiveria zizanioides, Alpinia galangal, Glycyrrhiza glabra, Inula racemosa*; seeds of *Elettaria cardamomum*; fruits of *Terminalia chebula, Terminalia bellerica, Piper nigrum* and *Piper longum*; heartwood of *Santalum album* and *Pterocarpus santalinus*; rhizome of *Zingiber officinale* and *Curcuma longa*; bark of *Cinnamomum zeylanica*; floral bud of *Syzygium aromaticum*; leaves of *Ocimum sanctum*; stem of *Tinospora cordifolia*; bark of *Cassia fistula*; fruit of *Embelia ribes*; heartwood of *Prunus cerasoides*; leaves of *Ricinus communis*; roots of *Boerhavia diffusa*; stem bark of *Terminalia arjuna*; oleo-gum-resin of *Commiphora mukul* (also referred to as Guggulu); and stamen of *Mesua ferrea*. However, it is also within the scope of the claims provided herein for the herbal composition to include other herb components such as leaf, flowers, etc. without otherwise departing from the intended function of the disclosed composition.

The herb components maybe included in the composition in any form that is generally known in the field. For example, the herb component may be fresh, dried, powdered, processed to form concentrates, extracts, sublimate etc. In an embodiment, the herb components are in the form of dry powder form which is incorporated into the composition. In an embodiment, the herb components are in the form of a fine powder that is obtained by 80 mesh size sieves. Although, the composition disclosed in the various embodiments herein includes dried and powdered form of specific herb components as disclosed herein, minor modifications and variations to form and components used would be apparent to a person skilled in the art.

The herbs used in the disclosed composition may be included as powders form of whole herb components, as extracts of herbs, or as active ingredients extracted from herbs. The extracts of herbs may be prepared by techniques known in the field and may include aqueous extracts, alcoholic extracts (e.g.: ethanolic or methanolic extracts) or a combination of aqueous and alcoholic extracts. In an embodiment, the composition includes aqueous ethanolic extracts of the herbs disclosed herein.

In an embodiment, the composition includes *Bacopa monnieri* in an amount ranging from 4 to 8 wt. %, *Convolvulus pluricaulis* in an amount ranging from 2 to 4 wt. %, *Mucuna pruriens* in an amount ranging from 2 to 4 wt. %, *Nardostachys jatamansi* in an amount ranging from 2 to 4 wt. %, *Rauwolfia serpentina* in an amount ranging from 2 to 4 wt. %, *Withania somnifera* in an amount ranging from 3 to 7 wt. %, *Acorus calamus* in an amount ranging from 2 to 4 wt. %, *Sida cordifolia* in an amount ranging from 2 to 4 wt. %, and *Emblica officinalis* in an amount ranging from 3 to 7 wt. %, of the total weight of the composition.

In another embodiment, the composition further includes at least one ingredient selected from a group consisting of *Santalum albumin* an amount of ≤2 wt %, *Pterocarpus santalinus* in an amount of ≤2 wt %, *Glycyrrhiza glabra* in an amount of ≤2 wt %, *Terminalia chebula* in an amount of ≤2 wt %, *Terminalia bellerica* in an amount of ≤2 wt %, *Zingiber officinale* in an amount of ≤2 wt %, *Piper nigrum* in an amount of ≤2 wt %, *Piper longum* in an amount of ≤2 wt %, *Curcuma longa* in an amount of ≤2 wt %, *Inula racemosa* in an amount of ≤2 wt %, *Cinnamomum zeylanica* in an amount of ≤2 wt %, *Elettaria cardamomum* in an amount of ≤2 wt %, *Syzygium aromaticum* in an amount of ≤2 wt %, *Ocimum sanctum* in an amount of ≤2 wt %, *Tinospora cordifolia* in an amount ranging from 1 to 3 wt. %, *Hemidesmus indicus* in an amount of ≤2 wt %, *Vetiveria zizanioides* in an amount of ≤2 wt %, *Alpinia galangal* in an amount ranging from 1 to 3 wt. %, *Cassia fistula* in an amount ranging from 1 to 3 wt. %, *Embelia ribes* in an amount of ≤2 wt %, *Prunus cerasoides* in an amount of ≤2 wt %, *Rubia cordifolia* in an amount of ≤2 wt %, *Ricinus communis* in an amount of ≤2 wt %, *Boerhavia diffusa* in an amount of ≤2 wt %, *Terminalia arjuna* in an amount of ≤2 wt %, *Commiphora mukul* in an amount of ≤2 wt %, *Picrorhiza kurroa* in an amount of ≤2 wt %, *Plumbago zeylanica* in an amount of ≤2 wt %, and *Mesua ferrea* in an amount of ≤2 wt %, of the total weight of the composition.

Minerals

The embodiments of the composition disclosed herein include minerals such as Shilajit (also known as oleo-gum-resin of *Asphaltum punjabianum*), Rasa sindura (the sublimed red sulfide of mercury) and Bhasmas. In an embodiment, the composition comprises of Shilajit. In an embodiment, the composition comprises of Rasa sindura. In another embodiment, the composition includes at least one bhasma selected from a group consisting of Swarna makshika bhasma, Loha Bhasma, Abhraka bhasma, Rajata Bhasma, Muktashukti Bhasma, Pravala Bhasma, Shringa Bhasma, Vanga Bhasma, Yashada Bhasma, Shankha Bhasma and Mandura Bhasma. Alternatively, the mineral element may also be selected from a group consisting of steel iron, swarna makshika (chalcopyrite), iron rust, zinc, tin, hart's horn, coral, pearl oyster, mercury, silver foil and mica. However, it is also within the scope of claims provided herewith for the disclosed composition to include, as a substitute or additionally, other similar calcined preparations or minerals without otherwise deterring from the intended function of the disclosed composition. The suitable standards of the ingredients used and modifications thereto that may be practiced would be apparent to a person skilled in the art.

In one embodiment, the composition includes Shilajit, Rasa sindura and at least one Bhasmas. In an embodiment, the composition includes Shilajit in an amount of ≤2 wt. % of the total weight of the composition. In an embodiment, the composition includes Rasa sindura in an amount of ≤2 wt. % of the total weight of the composition. In another embodiment, the composition includes at least one bhasma selected from a group consisting of Swarna makshika bhasma in an amount of ≤2 wt. %, Loha Bhasma in an amount of ≤2 wt. %, Abhraka bhasma in an amount of ≤2 wt. %, Rajata Bhasma in an amount of ≤2 wt. %, Mukta shukti Bhasma in an amount of ≤2 wt. %, Pravala Bhasma in an amount of ≤2 wt. %, Shringa Bhasma in an amount of ≤2 wt. %, Vanga Bhasma in an amount of ≤2 wt. %, Yashada Bhasma in an amount of ≤2 wt. %, Shankha Bhasma in an amount of ≤2 wt. % and Mandura Bhasma in an amount of ≤2 wt. %, of the total weight of the composition.

The disclosed composition, in the various embodiments herein, may further include one or more suitable excipient. The suitable excipients include solvents, binders, lubricants, herbal carriers, oils and salts that are generally known in the art. In an embodiment, the excipient includes acacia gum. The amount of *gum acacia* may be any amount suitable to perform the activity of an excipient. In an embodiment, the composition includes *gum acacia* in an amount in the range of 8 to 12 wt. % of the total weight of the composition.

Further, the amount of herb and mineral that may be included in the various embodiments of the disclosed composition may each be in the range of 0 to 15 wt %. In an embodiment, the composition includes *Bacopa monnieri* (4 to 8 wt. %), *Convolvulus pluricaulis* (2 to 4 wt. %), *Mucuna pruriens* (2 to 4 wt. %), *Nardostachys jatamansi* (2 to 4 wt. %), *Rauwolfia serpentina* (2 to 4 wt. %), *Withania somnifera* (3 to 7 wt. %), *Acorus calamus* (2 to 4 wt. %), *Sida cordifolia* (2 to 4 wt. %), *Emblica officinalis* (3 to 7 wt. %), and Shilajit (≤2 wt. %)

In another embodiment, the composition includes *Bacopa monnieri* (4 to 8 wt. %), *Convolvulus pluricaulis* (2 to 4 wt. %), *Mucuna pruriens* (2 to 4 wt. %), *Nardostachys jatamansi* (2 to 4 wt. %), *Rauwolfia serpentina* (2 to 4 wt. %), *Withania somnifera* (3 to 7 wt. %), *Acorus calamus* (2 to 4 wt. %), *Sida cordifolia* (2 to 4 wt. %), *Emblica officinalis* (3 to 7 wt. %), Rasa sindura (≤2 wt. %) and Shilajit (≤2 wt. %).

In another embodiment, the composition includes *Bacopa monnieri* (4 to 8 wt. %), *Convolvulus pluricaulis* (2 to 4 wt. %), *Mucuna pruriens* (2 to 4 wt. %), *Nardostachys jatamansi* (2 to 4 wt. %), *Rauwolfia serpentina* (2 to 4 wt. %), *Withania somnifera* (3 to 7 wt. %), *Acorus calamus* (2 to 4 wt. %), *Sida cordifolia* (2 to 4 wt. %), *Emblica officinalis* (3 to 7 wt. %) and Rasa sindura (≤2 wt. %).

In yet another embodiment, the composition includes *Bacopa monnieri* (4 to 8 wt. %), *Convolvulus pluricaulis* (2 to 4 wt. %), *Mucuna pruriens* (2 to 4 wt. %), *Nardostachys jatamansi* (2 to 4 wt. %), *Rauwolfia serpentina* (2 to 4 wt. %), *Withania somnifera* (3 to 7 wt. %), *Acorus calamus* (2 to 4 wt. %), *Sida cordifolia* (2 to 4 wt. %), *Emblica officinalis* (3 to 7 wt. %), Rasa sindura (≤2 wt. %), Shilajit (≤2 wt. %), Swarna makshika bhasma (≤2 wt. %), Loha Bhasma (≤2 wt. %), Abhraka bhasma (≤2 wt. %), Rajata Bhasma (≤2 wt. %), Muktashukti Bhasma (≤2 wt. %), Pravala Bhasma (≤2 wt. %), Shringa Bhasma (≤2 wt. %), Vanga Bhasma (≤2 wt. %), Yashada Bhasma (≤2 wt. %), Shankha Bhasma (≤2 wt. %), and Mandura Bhasma (≤2 wt. %).

In another embodiment, the composition includes *Bacopa monnieri* (4 to 8 wt. %), *Convolvulus pluricaulis* (2 to 4 wt. %), *Mucuna pruriens* (2 to 4 wt. %), *Nardostachys jatamansi* (2 to 4 wt. %), *Rauwolfia serpentina* (2 to 4 wt. %), *Withania somnifera* (3 to 7 wt. %), *Acorus calamus* (2 to 4 wt. %), *Sida cordifolia* (2 to 4 wt. %), *Emblica officinalis* (3 to 7 wt. %), *Santalum album* (≤2 wt. %), *Pterocarpus santalinus* (≤2 wt. %), *Glycyrrhiza glabra* (≤2 wt. %), *Terminalia chebula* (≤2 wt. %), *Terminalia bellerica* (≤2 wt. %), *Zingiber officinale* (≤2 wt. %), *Piper nigrum* (≤2 wt. %), *Piper longum* (≤2 wt. %), *Curcuma longa* (≤2 wt. %), *Inula racemosa* (≤2 wt. %), *Cinnamomum zeylanica* (≤2 wt. %), *Elettaria cardamomum* (≤2 wt. %), *Syzygium aromaticum* (≤2 wt. %), *Ocimum sanctum* (≤2 wt. %), *Tinospora cordi-* folia (1 to 3 wt. %), *Hemidesmus indicus* (≤2 wt. %), *Vetiveria zizanioides* (≤2 wt. %), *Alpinia galangal* (1 to 3 wt. %), *Cassia fistula* (1 to 3 wt. %), *Embelia ribes* (≤2 wt. %), *Prunus cerasoides* (≤2 wt. %), *Rubia cordifolia* (≤2 wt. %), *Ricinus communis* (≤2 wt. %), *Boerhavia diffusa* (≤2 wt. %), *Terminalia arjuna* (≤2 wt. %), *Commiphora mukul* (≤2 wt. %), *Picrorhiza kurroa* (≤2 wt. %), *Plumbago zeylanica* (≤2 wt. %), *Mesua ferrea* (≤2 wt. %), Rasa sindura (≤2 wt. %) and Shilajit (≤2 wt. %).

In yet another embodiment, the composition includes *Bacopa monnieri* (4 to 8 wt. %), *Convolvulus pluricaulis* (2 to 4 wt. %), *Mucuna pruriens* (2 to 4 wt. %), *Nardostachys jatamansi* (2 to 4 wt. %), *Rauwolfia serpentina* (2 to 4 wt. %), *Withania somnifera* (3 to 7 wt. %), *Acorus calamus* (2 to 4 wt. %), *Sida cordifolia* (2 to 4 wt. %), *Emblica officinalis* (3 to 7 wt. %), *Santalum album* (≤2 wt. %), *Pterocarpus santalinus* (≤2 wt. %), *Glycyrrhiza glabra* (≤2 wt. %), *Terminalia chebula* (≤2 wt. %), *Terminalia bellerica* (≤2 wt. %), *Zingiber officinale* (≤2 wt. %), *Piper nigrum* (≤2 wt. %), *Piper longum* (≤2 wt. %), *Curcuma longa* (≤2 wt. %), *Inula racemosa* (≤2 wt. %), *Cinnamomum zeylanica* (≤2 wt. %), *Elettaria cardamomum* (≤2 wt. %), *Syzygium aromaticum* (≤2 wt. %), *Ocimum sanctum* (≤2 wt. %), *Tinospora cordifolia* (1 to 3 wt. %), *Hemidesmus indicus* (≤2 wt. %), *Vetiveria zizanioides* (≤2 wt. %), *Alpinia galangal* (1 to 3 wt. %), *Cassia fistula* (1 to 3 wt. %), *Embelia ribes* (≤2 wt. %), *Prunus cerasoides* (≤2 wt. %), *Rubia cordifolia* (≤2 wt. %), *Ricinus communis* (≤2 wt. %), *Boerhavia diffusa* (≤2 wt. %), *Terminalia arjuna* (≤2 wt. %), *Commiphora mukul* (≤2 wt. %), *Picrorhiza kurroa* (≤2 wt. %), *Plumbago zeylanica* (≤2 wt. %), *Mesua ferrea* (≤2 wt. %), Rasa sindura (≤2 wt. %), Shilajit (≤2 wt. %), and at least one Bhasma (≤2 wt. %)

In another embodiment, the composition includes *Bacopa monnieri* (4 to 8 wt. %), *Convolvulus pluricaulis* (2 to 4 wt. %), *Mucuna pruriens* (2 to 4 wt. %), *Nardostachys jatamansi* (2 to 4 wt. %), *Rauwolfia serpentina* (2 to 4 wt. %), *Withania somnifera* (3 to 7 wt. %), *Acorus calamus* (2 to 4 wt. %), *Sida cordifolia* (2 to 4 wt. %), *Emblica officinalis* (3 to 7 wt. %), *Santalum album* (≤2 wt. %), *Pterocarpus santalinus* (≤2 wt. %), *Glycyrrhiza glabra* (≤2 wt. %), *Terminalia chebula* (≤2 wt. %), *Terminalia bellerica* (≤2 wt. %), *Zingiber officinale* (≤2 wt. %), *Piper nigrum* (≤2 wt. %), *Piper longum* (≤2 wt. %), *Curcuma longa* (≤2 wt. %), *Inula racemosa* (≤2 wt. %), *Cinnamomum zeylanica* (≤2 wt. %), *Elettaria cardamomum* (≤2 wt. %), *Syzygium aromaticum* (≤2 wt. %), *Ocimum sanctum* (≤2 wt. %), *Tinospora cordifolia* (1 to 3 wt. %), *Hemidesmus indicus* (≤2 wt. %), *Vetiveria zizanioides* (≤2 wt. %), *Alpinia galangal* (1 to 3 wt. %), *Cassia fistula* (1 to 3 wt. %), *Embelia ribes* (≤2 wt. %), *Prunus cerasoides* (≤2 wt. %), *Rubia cordifolia* (≤2 wt. %), *Ricinus communis* (≤2 wt. %), *Boerhavia diffusa* (≤2 wt. %), *Terminalia arjuna* (≤2 wt. %), *Commiphora mukul* (≤2 wt. %), *Picrorhiza kurroa* (≤2 wt. %), *Plumbago zeylanica* (≤2 wt. %), *Mesua ferrea* (≤2 wt. %), Rasa sindura (≤2 wt. %), Shilajit (≤2 wt. %), Swarna makshika bhasma (≤2 wt. %), Loha Bhasma (≤2 wt. %), Abhraka bhasma (≤2 wt. %), Rajata Bhasma (≤2 wt. %), Muktashukti Bhasma (≤2 wt. %), Pravala Bhasma (≤2 wt. %), Shringa Bhasma (≤2 wt. %), Vanga Bhasma (≤2 wt. %), Yashada Bhasma (≤2 wt. %), Shankha Bhasma (≤2 wt. %), and Mandura Bhasma (≤2 wt. %). All weight percentages are based on the total weight of the composition. However, it is apparent that slight variations and modifications in the amount of the ingredients may be practiced without otherwise departing from the intended function of the disclosed composition.

The herbal composition disclosed herein is best suited for oral administration and may be formulated accordingly into various suitable dosage forms. The herbal composition may be in the form of tablets, pellets, lozenges, granules, capsules, solutions, pellets, emulsions, suspensions, or any other form suitable for use. Generally known methods of formulating/processing ayurvedic compositions may be used to formulate the desired dosage forms. In an embodiment, the disclosed composition is formulated in the form of tablets, preferably 500 mg tablets. Table 1 is an exemplary embodiment depicting the quantities of each ingredient in a 500 mg tablet. Accordingly, embodiments disclosed herein include a tablet for treating cognitive dysfunction. In an embodiment, the tablet is a 500 mg tablet comprising ingredients as depicted in Table 1.

TABLE 1

Each 500 mg tablet includes:

| No. | Sanskrit Name | Part used | Latin/English name | Quantity |
|---|---|---|---|---|
| 1 | Brahmi | Dried whole plant | *Bacopa monnieri* | 32 mg |
| 2 | Shankhapushpa | Dried whole plant | *Convolvulus pluricaulis* | 16 mg |
| 3 | Kapikacchu | Dried seeds | *Mucuna pruriens* | 16 mg |
| 4 | Jatamansi | Dried rhizome | *Nardostachys jatamansi* | 16 mg |
| 5 | Sarpagandha | Dried root | *Rauwolfia serpentina* | 16 mg |
| 6 | Ashvagandha | Dried root | *Withania somnifera* | 25 mg |
| 7 | Vacha | Dried root | *Acorus calamus* | 16 mg |
| 8 | Amalaki | dry fruits | *Emblica officinalis* | 22 mg |
| 9 | Shveta Chandana | Dried heartwood | *Santalum album* | 6 mg |
| 10 | RaktaChandana | Dried heartwood | *Pterocarpus santalinus* | 6 mg |
| 11 | Yashtimadhu | Dried root | *Glycyrrhiza glabra* | 7.5 mg |
| 12 | Hareetaki | dry fruits | *Terminalia chebula* | 7 mg |
| 13 | Vibhitaki | dry fruits | *Terminalia bellerica* | 7 mg |
| 14 | Shunthi | Dry rhizome | *Zingiber officinale* | 7 mg |
| 15 | Mancha | Dry fruits | *Piper nigrum* | 7 mg |
| 16 | Pippali | dry fruits | *Piper longum* | 7 mg |

TABLE 1-continued

Each 500 mg tablet includes:

| No. | Sanskrit Name | Part used | Latin/English name | Quantity |
|---|---|---|---|---|
| 17 | Haridra | Dried rhizome | Curcuma longa | 7.5 mg |
| 18 | Pushkaramoola | Dried root | Inula racemosa | 6 mg |
| 19 | Bala | Dried root | Sida cordifolia | 15 mg |
| 20 | Tvak | Dried bark | Cinnamomum zeylanica | 6 mg |
| 21 | Ela | Dried seeds | Elettaria cardamomum | 6 mg |
| 22 | Lavanga | Dried floral bud | Syzygium aromaticum | 6 mg |
| 23 | Tulasi | Dried leaves | Ocimum sanctum | 6 mg |
| 24 | Guduchi | Dried stem | Tinospora cordifolia | 12 mg |
| 25 | Sariva | Dried root | Hemidesmus indicus | 6 mg |
| 26 | Ushira | Dried root | Vetiveria zizanioides | 6 mg |
| 27 | Rasna | Dried root | Alpinia galanga | 12 mg |
| 28 | Aragwadha | Dried bark | Cassia fistula | 12 mg |
| 29 | Vidanga | Dried fruit | Embelia ribes | 7.5 mg |
| 30 | Padmaka | Dried heartwood | Prunus cerasoides | 6 mg |
| 31 | Manjishtha | Dried root | Rubia cordifolia | 6 mg |
| 32 | Eranda | dried leaves | Ricinus communis | 6 mg |
| 33 | Punarnava | Dried root | Boerhavia diffusa | 6 mg |
| 34 | Arjuna | Dried stem bark | Terminalia arjuna | 6 mg |
| 35 | Shuddha Guggulu | Oleo-gum-resin | Commiphora mukul | 6 mg |
| 36 | Shilajit | Fossil resin | Asphaltum punjabianum | 8.5 mg |
| 37 | Katuki | Dried root | Picrorhiza kurroa | 5 mg |
| 38 | Chitraka | Dried root | Plumbago zeylanica | 5 mg |
| 39 | Nagakesara | Dried stamens | Mesua ferrea | 7.5 mg |
| 40 | Swarna Makshika bhasma | Incinerated ore | Incinerated copper pyrite | 6 mg |
| 41 | Loha Bhasma | Incinerated metal | Calx of iron | 6.5 mg |
| 42 | Abhraka bhasma | Incinerated mineral | Incinerated mica | 8.5 mg |
| 43 | Rajata Bhasma | Incinerated silver | Calx of silver | 2 mg |
| 44 | Muktashukti Bhasma | Incinerated mineral | Incinerated pearl oyster | 6 mg |
| 45 | Pravala Bhasma | Incinerated mineral | Incinerated coral | 6 mg |
| 46 | Rasa sindura | Sublimed Product | Mercury sulphide-hexagonal | 8.5 mg |
| 47 | Shringa Bhasma | Incinerated animal product | Calx of Hart's horn | 6 mg |
| 48 | Vanga Bhasma | Incinerated metal | Calx of tin | 4.25 mg |
| 49 | Yashada Bhasma | Incinerated metal | Calx of Zinc | 4.25 mg |
| 50 | Shankha Bhasma | Incinerated mineral | Calx of conch shell | 6 mg |
| 51 | Mandura Bhasma | Incinerated mineral | Calx of iron rust | 2.5 mg |
| 52 | Excipient | Resin | Gum acacia | 50 mg |

The disclosed composition (as disclosed in Table 1) was analyzed for parameters including physicochemical properties such as Tablet hardness, Loss on drying, Assay, Disintegration time, Ash value, etc and the results were noted. Table 2 depicts the results of the analysis performed to determine the physicochemical properties. In an embodiment, the disclosed tablets have the characteristics as depicted in Table 2. It will be apparent to those skilled in the art that many modifications, both to materials and methods, may be practiced without departing from the scope of the claims herein.

TABLE 2

| TEST PARAMETERS | SPECIFICATIONS |
|---|---|
| Description | Blackish brown biconvex shaped tablets |
| Identification | Tests positive for saponins, alkaloids, glycosides and tannins, TLC of unique pattern with peaks comparable to Bacopaside, Piperine |
| Average weight | 500 mg ± 12.5 mg |
| Uniformity of weight | ±2.5% of actual average weight |

TABLE 2-continued

| TEST PARAMETERS | SPECIFICATIONS |
| --- | --- |
| Average tablet hardness | 4.1 kg/cm$^2$ |
| Loss on drying | 3.2% w/w |
| Water soluble extractive | 25-31% w/v |
| Methanol soluble extractive | 7-11% w/v |
| Chloroform soluble extractive | 3-5% w/v |
| Ash value | 18.0% w/w |
| Average Disintegration time | 16 minutes |

Method

Disclosed herein are embodiments of a method for the preparation of the disclosed composition. In an embodiment, the method includes:

preparing a grinding decoction;

levigating at least one ingredient selected from a group consisting of bhasmas, Rasa sindura, Guggulu and Shilajit with a first portion of said grinding decoction in a grinder;

adding powdered herbs into said grinder and grinding with a second portion of said grinding decoction, to obtain a homogenous mass.

In an embodiment, the method of preparation further includes mixing the obtained composition with a suitable excipient and grinding to obtain a semisolid mass. The obtained semisolid mass may further be processed by methods known in the field to obtain oral dosage forms. In an embodiment, the method of preparation further includes drying at 55 to 65 degrees Celsius, granulating and punching to obtain tablets. In an embodiment, the method includes drying the obtained mass at a temperature of 60 degrees Celsius in a hot air oven, granulating by wet granulation and punching to obtain 500 mg tablets. Granulation and tablet punching may be performed according to methods generally known in the field. FIG. 1 depicts a flowchart for the preparation of fortified tablets. All raw materials such as herbs and minerals instrumental in the various embodiments herein are of genuine purity whose identity and quality are confirmed by traditional experts and are as per generally acceptable standards. The raw materials instrumental in the various embodiments herein are subjected to appropriate cleaning procedures that are considered standard and acceptable in the field. In an embodiment, the raw materials were subjected to cleaning with potable mineral water prior to its use.

Preparation of Grinding Decoction:

In the various embodiments disclosed herein, the grinding decoction is a decoction of herbs that facilitates grinding. The grinding decoction provides lubrication and improves binding of the ingredients. In an embodiment, the grinding decoction includes a decoction of at least one herb selected from a group consisting of: *Aloe vera, Centella asiatica, Stereospermum suaveolens, Premna mucronata, Gmelina arborea, Aegle marmelos, Oroxylum indicum, Desmodium gangeticum, Uraria picta, Solanum indicum, Solanum xanthocarpum, Tribulus terrestris, Acorus calamus, Celastrus paniculatus, Nardostachys jatamansi, Rauwolfia serpentina, Alpinia galanga, Asparagus racemosus, Triticum aestivum, Cuminum cyminum, Coriandrum sativum, Apium graveolens, Yavakshara alkali* (Alkali of *Hordeum vulgare*), *Sarjikshara alkali* (Barilla), and *Cissus quadrangularis*. In an embodiment, one part of each of the ingredients viz. *Aloe vera, Centella asiatica, Stereospermum suaveolens, Premna mucronata, Gmelina arborea, Aegle marmelos, Oroxylum indicum, Desmodium gangeticum, Uraria picta, Solanum indicum, Solanum xanthocarpum, Tribulus terrestris, Acorus calamus, Celastrus paniculatus, Nardostachys jatamansi, Rauwolfia serpentina, Alpinia galanga, Asparagus racemosus, Triticum aestivum, Cuminum cyminum, Coriandrum sativum, Apium graveolens, Yavakshara alkali* (Alkali of *Hordeum vulgare*), *Sarjikshara alkali* (Barilla), and *Cissus quadrangularis* are used to prepare the grinding decoction.

The herb ingredients used in the preparation of grinding decoction may be included as a whole or in parts such as leaves, roots, stem, fruits, seeds, etc. The ingredients that are used may comprise of herbs in dry or fresh form. In an embodiment, said herb ingredients include coarsely powdered form of herbs that is sieved through a 10-mesh screen. In an embodiment, the ingredients include coarsely powdered form of the following ingredients: fresh leaves of *Aloe vera*, fresh leaves of *Centella asiatica*, dry root of *Stereospermum suaveolens*, dry root of *Premna mucronata*, dry root of *Gmelina arborea*, dry root of *Aegle marmelos*, dry root of *Oroxylum indicum*, dry plant of *Desmodium gangeticum*, dry plant of *Uraria picta*, dry root of *Solanum indicum*, dry plant of *Solanum xanthocarpum*, dry fruit of *Tribulus terrestris, Acorus calamus, Celastrus paniculatus, Nardostachys jatamansi, Rauwolfia serpentina, Alpinia galanga*, fresh root of *Asparagus racemosus*, fresh leaves of *Triticum aestivum*, dry seeds of *Cuminum cyminum*, dry fruits of *Coriandrum sativum*, dry seeds of *Apium graveolens*, and fresh stem of *Cissus quadrangularis; Yavakshara alkali* (Alkali of *Hordeum vulgare*) and *Sarjikshara alkali* (Barilla). *Yavakshara alkali* (Alkali of *Hordeum vulgare*) and *Sarjikshara alkali* (Barilla) may be prepared by methods generally known in the field. For example: Acharya Sadananda Sharma, Rasatarangini, Pandit Kashinath Shastri, Tarang 13/3-5, Chaukhambha Sanskrit Bhavan, Varanasi, Reprint, 2014; and Acharya Sadananda Sharma, Rasatarangini, Pandit Kashinath Shastri, Tarang 13/45-47, Chaukhambha Sanskrit Bhavan, Varanasi, Reprint, 2014.

In an embodiment, the grinding decoction includes coarsely powdered form of the following ingredients: 3 parts of fresh leaves of *Aloe vera*, 3 parts of fresh leaves of *Centella asiatica*, ½ part of dry root of *Stereospermum suaveolens*, ½ part of dry root of *Premna mucronate*, ½ part of dry root of *Gmelina arborea*, ½ part of dry root of *Aegle marmelos*, ½ part of dry root of *Oroxylum indicum*, ½ part of dry plant of *Desmodium gangeticum*, ½ part of dry plant of *Uraria picta*, ½ part of dry root of *Solanum indicum*, ½ part of dry plant of *Solanum xanthocarpum*, ½ part of dry fruit of *Tribulus terrestris*, 2 part of *Acorus calamus*, 2 part of *Celastrus paniculatus*, 2 part of *Nardostachys jatamansi*, 3 part of *Rauwolfia serpentina*, 2 part of *Alpinia galanga*, 1 part fresh roots of *Asparagus racemosus*, 1 part of fresh leves of *Triticum aestivum*, 0.4 part of dry seeds of *Cuminum cyminum*, 0.4 part of dry fruits of *Coriandrum sativum*, 0.4 part of dry seeds of *Apium graveolens*, 0.3 part of *Yavakshara alkali* (Alkali of *Hordeum vulgare*), 0.3 part of *Sarjikshara alkali* (Barilla), 0.8 part of fresh stem of *Cissus quadrangularis* and 427.2 parts of water. Table 3 depicts the Grinding ingredients required for Grinding decoction.

The decoction may be obtained by any method of decocting generally known in the field. In an embodiment, the method of preparation of grinding decoction includes, soaking the ingredients in water, i.e. fresh leaves of *Aloe vera*, fresh leaves of *Centella asiatica*, dry root of *Stereospermum suaveolens*, dry root of *Premna mucronata*, dry root of *Gmelina arborea*, dry root of *Aegle marmelos*, dry root of *Oroxylum indicum*, dry plant of *Desmodium gangeticum*, dry plant of *Uraria picta*, dry root of *Solanum indicum*, dry plant of *Solanum xanthocarpum*, dry fruit of *Tribulus terrestris, *Acorus calamus, Celastrus paniculatus, Nardostachys jatamansi, Rauwolfia serpentina, Alpinia galanga*, fresh root of *Asparagus racemosus*, fresh leaves of *Triticum aestivum*, dry seeds of *Cuminum cyminum*, dry fruits of *Coriandrum sativum*, dry seeds of *Apium graveolens*, Yavakshara alkali (Alkali of *Hordeum vulgare*), Sarjikshara alkali (Barilla) and fresh stem of (*Cissus quadrangularis*); and boiling to obtain a decoction In an embodiment, soaking may be performed by soaking the grinding herbs in 16 parts of water for a period of 5 to 15 hours or overnight. In one embodiment, boiling is performed at a high temperature of 80 to 85 degree Celsius, until amount of liquid is reduced to $1/8^{th}$ of the initial volume. The grinding decoction may be filtered before use. The grinding decoction may further be apportioned into two or three portions. The first portion may be used in levigation. The second portion of the grinding decoction may be used to grind the levigated mixture and powdered herbs. *Gum acacia* may be added into the composition by dissolving in a third portion of the grinding decoction which may be added to the obtained homogenous mass. Alternatively, *Gum acacia* may be dissolved in the second portion of grinding decoction and added to the powdered herbs while grinding. It would be apparent to a person skilled in the art that the portion size, number, etc are aspects which are flexible and may vary depending on requirement and convenience.

Table 3 is an exemplary embodiment depicting the herb ingredients used in the preparation of grinding decoction.

TABLE 3

List of Grinding herbs
Decoction of following herbs:

| | | | |
|---|---|---|---|
| 1 | Kumari fresh leaf | *Aloe vera* | 3 parts |
| 2 | Mandookaparni fresh leaves | *Centella asiatica* | 3 parts |
| 3 | Patala dry root | *Stereospermum suaveolens* | ½ part |
| 4 | Agnimantha dry root | *Premna mucronata* | ½ part |
| 5 | Gambhari dry root | *Gmelina arborea* | ½ part |
| 6 | Bilva dry root | *Aegle marmelos* | ½ part |
| 7 | Shyonaka dry root | *Oroxylum indicum* | ½ part |
| 8 | Shalaparni dry plant | *Desmodium gangeticum* | ½ part |
| 9 | Prshniparni dry plant | *Uraria picta* | ½ part |
| 10 | Brhati dry root | *Solarium indicum* | ½ part |
| 11 | Kantakari dry plant | *Solanum xanthocarpum* | ½ part |
| 12 | Gokshura dry fruit | *Tribulus terrestris* | ½ part |
| 13 | Vacha | *Acorus calamus* | 2 parts |
| 14 | Jyotishmati | *Celastrus paniculatus* | 2 parts |
| 15 | Jatamansi | *Nardostachys jatamansi* | 2 parts |
| 16 | Sarpagandha | *Rauwolfia serpentina* | 3 parts |
| 17 | Rasna | *Alpinia galanga* | 2 parts |
| 18 | Shatavari fresh root | *Asparagus racemosus* | 1 part |
| 19 | Godhuma fresh leaves | *Triticum aestivum* | 1 part |
| 20 | Jeeraka dried seeds | *Cuminum cyminum* | 0.4 part |
| 21 | Dhanyaka dried fruits | *Coriandrum sativum* | 0.4 part |
| 22 | Ajamoda dried seeds | *Apium graveolens* | 0.5 part |
| 23 | Yavakshara alkali | Alkali of *Hordeum vulgare* | 0.3 part |
| 24 | Sarjikshara alkali | Barilla | 0.3 part |
| 25 | AsthiShrinkhala fresh stem | *Cissus quadrangularis* | 0.8 part |
| 26 | Jala Avashesha (Reduced to) | Water | 427.2 parts ⅛ part of water |

Levigation:

In the various embodiments disclosed herein, levigation of said mixture comprising Bhasmas, Rasa sindura, Guggulu and Shilajit, may be performed by methods generally known in the field. In an embodiment, said levigation is performed by grinding said mixture of Bhasmas, Rasa sindura, Guggulu and Shilajit in a grinder with a first portion of grinding decoction for a duration of about 1 to 4 hours to obtain a levigated mixture. In an embodiment, levigation is performed for a duration of 3 hours. The mixture of bhasmas, Rasa sindura, Guggulu and Shilajit instrumental in the embodiments herein may be in a form that facilitates levigation. In an embodiment, said Guggulu and Shilajit are dissolved in the first portion of grinding decoction prior to levigation with Rasa sindura. In another embodiment, the grinding decoction is directly added to a mixture comprising bhasma, Shilajit, Rasa sindura and Guggulu during levigation.

The bhasmas that are used in the various embodiments of the disclosed herbal composition may be prepared by methods that are generally known in the field. The bhasmas may be prepared by a process comprising of the steps of Shodhana or Purification; Trituration; and Marana or Incineration. In an embodiment, the process for preparation of Bhasmas includes: selecting a mineral; purifying the mineral; triturating the purified mineral; and incinerating to obtain bhasma.

Selection of a Mineral:

In an embodiment, said mineral is genuine standard mineral such as steel iron, swarna makshika (chalcopyrite), iron rust, zinc, tin, hart's horn, coral, pearl oyster, silver foil or mica, whose identity and quality has been confirmed by in-house traditional experts. In an embodiment, the selected mineral is further cleaned with potable mineral water; and dried at a temperature of about 50 degree Celsius. Drying of the mineral in the various embodiments herein may be achieved by drying in a hot air oven at a temperature of about 50 degree Celsius; or by exposure to sunlight.

Purification of Mineral:

The purification (also referred to as Shodhana) of the mineral may be performed by generally known methods in the field such as triturating, quenching, boiling, etc. In an embodiment, said purification of mineral includes general purification (also referred to as Samanya shodhana) and Special purification (also referred to as Vishesha shodhana). In another embodiment, purification may be a single step process involving boiling, quenching and/or trituration.

Trituration of Purified Mineral:

Trituration of the mineral may be performed by generally known methods in the field. In an embodiment, trituration is performed by grinding the mineral with herbal decoction. In another embodiment, trituration is performed by grinding the mineral with herbal juice. The herbal decoction or herbal juice used for triturating include any herbal decoction/juice that is generally used for triturating in the preparation of bhasmas such as Triphala, Lemon juice, *Aloe vera* juice etc. In an embodiment, trituration is performed by grinding the mineral with Gomutra (cow's urine). Trituration may be performed until a homogenous mixture having reduced particle size is obtained.

Incineration:

Incineration of the mineral may be performed by methods generally known in the field. In an embodiment, incineration is performed by putta system. In an embodiment, said incineration of mineral includes preparing discs of the mineral; and subjecting said discs to a specific quantum and pattern of heat to obtain incinerated mineral powder or bhasma. In an embodiment, said discs have a thickness of about 0.5 cm thickness and a diameter of about 2.5 cm. The prepared discs may further be dried at a temperature of about 50 degree Celsius. The discs may be exposed to sunlight or exposed to a temperature of about 50 degrees Celsius in a hot air oven. The discs of mineral are further subjected to heat by sealing inside a capsule made using earthern saucers also known as the puta system of heating which includes preparation of Sharava Samputa and heating in Gaja puta, Ardha Gaja puta, Kukkuta puta, Laghu puta, etc. The incinerated mineral powder is further powdered and used as bhasma. In an embodiment, the incinerated mineral powder may again be subjected to repeated rounds of trituration and incineration in order to obtain a Bhasma. In an embodiment, the procedure may be repeated for about 7 to 30 times in order to obtain Bhamsa.

Embodiments are further described herein by reference to the working examples provided hereunder. The following examples are included herein by way of illustration only and should not be construed to limit the scope of the claims provided herewith.

Mandura Bhasma:

Mandura bhasma may be prepared by methods generally known in the field. The mineral or starting material used in the preparation of Mandura bhasma in the various embodiments herein include iron rust, preferable iron rust (oxidized iron) which is at least 60 years, (also referred to as "Mandura"). The starting material is further purified, triturated and incinerated to obtain Mandura Bhasma. The process for the preparation of Mandura bhasma includes cleaning and drying Mandura, purifying said Mandura by Samanya Shodhana (General purification) and Vishesha Shodhana, (Special purification), exposing to sun light by Bhanupaka, triturating with Triphala decoction and Cow's urine, and incinerating by putta system to obtain a powder or bhasma. The obtained powder is subjected to the putta system of incineration by generally known methods. The obtained powder may further be triturated with Triphala decoction and Cow's urine and incinerated again to obtain bhasma. The trituration and incineration process may further be repeated in many cycles to obtain a Bhasma. In an embodiment, the obtained powder is triturated and incinerated for 3 cycles in order to obtain Mandura Bhasma. Further, Samanya Shodhana, Vishesha Shodhana and Bhanupaka of the mineral may be performed by methods generally known in the field. Samanya Shodhana includes heating the mineral until it turns red hot followed by dipping in 5 different liquid media, separately, such as sesame oil, butter milk, cow urine, Kanji (also known as "Kanjika" or sour medicated rice gruel) and Horse gram decoction. Samanya Shodhana is repeated 7 times in each liquid. In another embodiment, said Vishesha Shodhana includes heating the mineral until red hot and then immersing the mineral in Triphala decoction.

Bhanupaka of mineral includes adding Triphala decoction to purified Mandura and exposing it to sunlight until complete evaporation occurs. Bhanupaka is repeated 7 times.

Example 1: Preparation of Mandura Bhasma

Iron rust, the raw material, was obtained from authorized supplier. X Ray diffraction study confirmed that the raw Mandura contained $Fe_2SiO_4$. The raw Mandura was heated till red hot (630° C. temp) and dipped in 5 different liquid media namely: sesame oil, butter milk, cow urine, Kanji and Horse gram decoction, to obtain "Samanya shodhita Mandura". The process was repeated 7 times in each liquid media. The samanya shodhita Mandura was heated to red hot and then immersed in Triphala decoction. Triphala Decoction was prepared by boiling 1 part of Triphala and 8 parts of water until the solution was reduced to ¼th of original quantity. Mandura was mixed with Triphala decoction and kept under sun light until complete evaporation of liquid occurred. Upon complete drying of mixture, the decoction of Triphala was added again and dried under sun light. This process was repeated 7 times. The purified and sundried material was triturated with cow urine and triphala decoction using mortar and pestle. The triturated doughy mass obtained was made into discs of 0.5 cm×2.5 cm size and dried. These dried discs were sealed in earthen saucers (1-2 layers) to form a capsule. This capsule was subjected to Gaja Puta (here, in a pit of 56.26×56.25×56.25 cubic cm, 250 cow dungs cakes of standard size were filled; earthen capsule was placed on it. Vacant space was again filled with 125 cow dungs cakes and lit with fire. (Here, specific quantum and pattern of heating was provided.). After self-cooling (cooling by itself, without any external aid), earthen saucer capsule was carefully collected, seal was removed, saucers separated and the material inside was collected. This procedure of levigation and incineration was repeated three times till a very fine Mandura Bhasma was formed.

Loha Bhasma:

Loha bhasma may be prepared by methods generally known in the field. The mineral or starting material used in the preparation of Loha bhasma in the various embodiments herein include Steel iron, (also referred to as "Loha"). The starting material is further purified, triturated and incinerated to obtain Loha Bhasma. The process of preparation of Loha bhasma includes cleaning and drying the mineral, purifying said mineral, triturating with herbal decoction and/or herbal juices, and incinerating by putta system to obtain a powder or bhasma. The obtained powder is subjected to the putta system of incineration by generally known methods. The trituration and incineration process of the obtained powder may further be repeated in many cycles to obtain Loha Bhasma. In an embodiment, the obtained powder is triturated and incinerated for 30 cycles in order to obtain Loha Bhasma. In an embodiment, said purification process of the mineral includes quenching the mineral in Triphala decoction. The herbal decoction/juice used in the trituration process of Loha bhasma includes a decoction of at least one of the following ingredients: *Emblica officinalis, Terminalia chebula, Terminalia bellerica, Crataeva nurvala, Boerhavia diffusa, Bauhinia variegate* and Cow urine. Table 4 depicts the ingredients of the herbal decoction used in the preparation of Loha bhasma.

TABLE 4

Herbal decoction used for trituration while preparing Loha Bhasma. Decoction of following herbs:

| | | | |
|---|---|---|---|
| 1. | Amalaki | *Emblica officinalis* | 1 part |
| 2. | Hareetaki | *Terminalia chebula* | 1 part |
| 3. | Vibheetaki | *Terminalia bellerica* | 1 part |
| 4. | Varuna | *Crataeva nurvala* | 1 part |
| 5. | Punarnava | *Boerhavia diffusa* | 1 part |
| 6. | Kanchanara | *Bauhinia variegata* | 1 part |
| 7. | Gomutra | Cow urine | 48 parts |
| 8. | Jala | Water | 48 parts |
| | Avashesha (Reduced to) | | 1/8 part of liquid |

Example 2: Preparation of Loha Bhasma

Specific quantity of raw material (Fe turning) was heated in Electric Muffle Furnace until red hot condition (~875-900° C.) and immersed in each medium viz. tila taila (sesame oil), takra (buttermilk), Gomutra (cow's urine), kanji (sour rice gruel), and kulattha kwatha (decoction of horse gram) and kept for self-cooling (approximately 1 h) at room temperature). This quenching process was repeated seven times consecutively in each of tila taila, takra, gomutra, kanji, and kulattha kwatha by using fresh media every time. After completion of the process, material was filtered by iron mesh and dried under sunlight. The material obtained at this stage is called samanya shodhita lauha. The mineral was further purified by quenching in Triphala kwatha. Triphala kwatha was prepared by taking coarse powders of three myrobalans, taken without seed, namely Haritaki (*Terminalia chebula* Retz.), Bibhitaki (*Terminalia bellerica* [Gaertn.] Roxb.), and Amalaki (*Phyllanthus emblica* L.) in equal quantity and boiled in 8 times of water until reduction to ¼th of the original volume of liquid was achieved. Repeated quenching of samanya shodhita lauha in Triphala kwatha was performed for about seven times using freshly prepared Triphala kwatha each time. The lauha churna (coarse powder of Fe turning) obtained at this stage is called vishesha shodhita lauha. For Bhanupaka, Triphala kwatha was prepared by heating equal quantities of Triphala and vishesha shodhita lauha churna with two parts of water and reducing the liquid by boiling to ¼th of the original volume. This Triphala kwatha was then added to lauha obtained after vishesha shodhana and allowed to dry under sunlight. For the step of Sthalipaka, Triphala kwatha was prepared by boiling Triphala in an amount 3 times as that of lauha obtained after bhanupaka and 16 times of water. The whole mixture was boiled in a stainless-steel container to reduce the volume to ⅛th of the original volume of water. Lauha obtained after bhanupaka was washed with hot water and placed in an iron pan (sthali), to which above freshly prepared Triphala kwatha was added and intense heating was performed until complete evaporation of water contents was achieved. On complete drying of the material, again Triphala kwatha was added and subjected to heat until dryness. For Putapaka, freshly prepared Decoction as mentioned in Table 4 was mixed with the powder obtained after Sthali Paka in mechanized khalva yantra (mortar and pestle) and trituration was done with a frequency of 60 times/min. The paste formed during this trituration was made into cakrikas (pellets) and dried under sunlight. After complete drying of cakrikas, it was taken in an earthen vessel (sarava) and covered with another inverted earthen vessel. The space between the two earthen vessels was covered with clay smeared cloth; this specific process was known as Sarava samputikarana (sealed earthen saucers). Dried earthen capsule containing the discs was subjected to heat using Gaja Puta (here, in a pit of 56.26×56.25×56.25 cubic cm, 250 cow dungs cakes of standard size were filled; earthen capsule was placed on it. Vacant space was again filled with 125 cow dungs cakes and lit with fire. (Here, specific quantum and pattern of heating was provided.). After self-cooling (cooling by itself, without any external aid), earthen saucer capsule was carefully collected, seal was removed, saucers separated and the material inside was collected. This procedure of grinding with decoction and heating was repeated at least 30 times or until the Bhasma was properly prepared which was ascertained by specific tests that are generally known in the field.

Vanga Bhasma:

Vanga bhasma may be prepared by methods generally known in the field. The mineral or starting material used in the preparation of Vanga bhasma in the various embodiments herein is Tin. The starting material is further purified, triturated and incinerated to obtain Vanga Bhasma. In an embodiment, the process of preparation of Vanga bhasma includes cleaning and drying the mineral, purifying said mineral, triturating with herbal decoction and/or herbal juices, and incinerating by putta system to obtain a powder or bhasma. The obtained powder is subjected to the putta system of incineration by generally known methods. The trituration and incineration process of the obtained powder may further be repeated in many cycles to obtain Vanga Bhasma. In an embodiment, the obtained powder is triturated and incinerated for 16 cycles in order to obtain Vanga Bhasma. In an embodiment, said purification of the mineral includes melting the mineral, and pouring in lime water. The process of purification may be repeated seven times to obtain purified mineral. The mineral may further be treated with *Achyranthes aspera*. In an embodiment, poling of the mineral is performed with green *Achyranthes aspera* to get a partially oxidized powder which is used for trituration. The herbal decoction/juice used in the preparation of Vanga bhasma includes decoction of at least one of the following herbs: *Aloe vera, Musa sapientum* and *Vitex negundo*. Table 5 depicts the ingredients of the herbal decoction used in the preparation of Vanga bhasma

TABLE 5

Herbal decoction used for trituration while preparing Vanga Bhasma. Juice of following herbs:

| 1. | Kumari leaf juice | *Aloe vera* | 1 part |
| 2. | Kadali root juice | *Musa sapientum* | 1 part |
| 3. | Nirgundi leaf juice | *Vitex negundo* | 1 part |

Example 3: Preparation of Vanga Bhasma 99.9% pure tin bars certified for purity by ICP-OES were collected. The raw vanga (tin) was heated to melt and then quenched sequentially in each of the following media: sesame oil, buttermilk, cow's urine, kanji, kullatha kwatha. Quenching was performed 7 times in each, using fresh media each time. In vishesha shodhana, Vanga processed in previous step was melted and quenched in lime water, followed by washing in hot water and then dried. This procedure was repeated seven times, each time using fresh batch of lime water. The shodhita (Purified) Vanga was put in an iron vessel and heated over flame until it melted. Then one forth part of coarse powder of dried whole plant of Apamarga (*Achyranthes aspera*) was added to the molten Vanga and stirred with iron ladle. The process was repeated till the whole of Vanga was converted into powder form. The powder was then covered with an earthen saucer and heated strongly for about 30 mins. Once heated, it was allowed to cool and further collected. Powdered Vanga from Jarana steps was triturated with the freshly extracted juice of *Aloe vera* Torun ex-Linn (Kumari Swarasa) juice in mortar with the help of pestle until a thick paste was formed which is suitable for making pellets (Chakrikas). Pellets of 0.5 cm thickness and 2.5 cm diameter were made and dried under Sun or/in hot air oven at 50° C. Dried discs were spread as a layer in an earthen saucer (Sharava). It was closed with another earthen saucer. The joint between the earthen saucers was sealed with mud plasters and dried to get a capsule (Sharava samputa). The incineration with traditional method of heating was carried out using kukkuta puta, the [pit of 45 cm (1×b×h)] and 60 cow dung cakes. This process was repeated four times using the liquids mentioned in Table 5. After complete incineration the white colored Vanga Bhasma was obtained.

Abhraka Bhasma:

Abhraka bhasma may be prepared by methods generally known in the field. The mineral or starting material used in the preparation of Abhraka bhasma in the various embodiments herein is Mica. The starting material is further purified, triturated and incinerated to obtain Abhraka Bhasma. In an embodiment, the process of preparation of Vanga bhasma includes cleaning and drying the mineral, purifying said mineral, triturating, and incinerating by putta system to obtain a powder or bhasma. The obtained powder is subjected to the putta system of incineration by generally known methods. The trituration and incineration process of the obtained powder may further be repeated in many cycles to obtain Abhraka Bhasma. In an embodiment, the obtained powder is triturated and incinerated for 30 cycles in order to obtain Abhraka Bhasma. In an embodiment, said purification of the mineral includes quenching the mineral in Cow's milk. The purified mineral may further be bundled in woolen cloth, dipped in water and squeezed to obtain microfine particles. The herbal decoction/juice used in the preparation of Abhraka bhasma are provided in Table 6 and Table 7. The triturated mineral is subjected to the putta system of incineration by generally known methods. The powder obtained after incineration is used as Abhraka Bhasma.

TABLE 6

Herbal decoction used for trituration while preparing Abhraka Bhasma includes the following:
Decoction of following:

| | | | |
|---|---|---|---|
| 1. | Amalaki dried fruit | *Emblica officinalis* | 1 part |
| 2. | Hareetaki dried fruit | *Terminalia chebula* | 1 part |
| 3. | Vibheetaki dried fruit | *Terminalia bellerica* | 1 part |
| 4. | Musta dried rhizome | *Cyperus rotundus* | 1 part |
| 5. | Vata dried root bark | *Ficus benghalensis* | 1 part |
| 6. | Haridra dried rhizome | *Curcuma longa* | 1 part |
| 7. | Jala | Water | 96 parts |
| | Avashesha (Reduced to) | | 1/8 part of liquid |

TABLE 7

Herbal juice used in trituration while preparing Abhraka Bhasma includes the following:
Juice of following:

| | | | |
|---|---|---|---|
| 1. | Kasamarda fresh leaves | *Cassia occidentalis* | 1 part |
| 2. | Tambula fresh leaves | *Piper betle* | 1 part |
| 3. | Vasa fresh leaves | *Adhatoda vasica* | 1 part |
| 4. | Amalaki fresh fruit | *Emblica officinalis* | 1 part |
| 5. | Matsyakshi fresh plant | *Alternanthera sessilis* | 1 part |
| 6. | Tanduleeyaka fresh plant | *Amaranthus spinosus* | 1 part |
| 7. | Eranda fresh leaves | *Ricinus communis* | 1 part |
| 8. | Arka fresh leaves | *Calotropis procera* | 1 part |

Example 4: Preparation of Abhraka Bhasma

The raw material, Abhraka (Biotite), and other ingredients were procured from known authentic sources and thoroughly screened by Rasashastra experts based on the Grahya Lakshanas (ideal characteristics) mentioned in the classics. The raw material was then subjected to purification (Shodhana of Abhraka). Specific quantity of Biotite mica was subjected to Shodhana by Nirvapa process (i.e. Heating & Quenching in liquid media) with the help of Triphala kwath (decoction of Triphala i.e. *Emblica officinalis, Terminalia chebula* and *Terminalia bellerica*) for 7 times. Each time fresh Triphala kwath was used for quenching, average temperature at the red-hot stage of Abhraka was around 739.00° C. After the Shodhan process, purified mica was mixed with ¼ part of Dhanya (Unhusked rice-paddy) taken in a jute bag and tied into a bolus. This bolus (Pottali) was then immersed in a big stainless-steel vessel containing Kanji (sour gruel) and kept for 3 days (72 hours). On the 4$^{th}$ day the jute bag was opened and vigorously rubbed in Kanji with both the hands until all Abhraka particles came out through pores of jute bag. It is allowed to settle down, kanji was decanted from vessel and Abhraka powder was collected which is referred as Dhanyabhraka. The obtained Dhanyabhraka was then incinerated (Marana). For incineration, the Dhanyabhraka is levigated using mortar and pestle with specific decoction/juice (provided in Table 6& Table 7) in equal quantity by weight for at least 6 hrs. until a homogeneous paste was formed, from which pellets (discs) were made of uniform size & shape (0.5×2.5 cm). Discs were dried under Sun or/in hot air oven at about 50° C. Dried discs were subjected to putta system of incineration. The saucers are allowed to cool. After self-cooling (cooling by itself, without any external aid), earthen saucer capsule was carefully collected, seal was removed, saucers separated and the material inside was collected. Content inside the earthen saucer capsule was powdered and levigated again with herbal decoction/juice (provided in Table 6& Table 7). This cycle of levigation and incineration was repeated at least 30 times or until the Bhasma was properly prepared which is ascertained by specific generally known tests.

Muktashukti Bhasma:

Muktashukti bhasma may be prepared by methods generally known in the field. The mineral or starting material used in the preparation of Muktashukti bhasma in the various embodiments herein is Pearl oyster. The starting material is further purified, triturated and incinerated to obtain Muktashukti Bhasma. In an embodiment, the process of preparation of Muktashukti bhasma includes cleaning and drying the mineral, purifying said mineral, triturating with herbal decoction and/or herbal juices, and incinerating by putta system to obtain a powder or bhasma. The obtained powder is subjected to the putta system of incineration by generally known methods. The trituration and incineration process of the obtained powder may further be repeated in many cycles to obtain Muktashukti Bhasma. In an embodiment, the obtained powder is triturated and incinerated for 2 cycles in order to obtain Muktashukti Bhasma. In an embodiment, said purification of the mineral includes boiling the mineral in Kanjika for a period of about 6 hours. The mineral may further be dried at a temperature of about 70 degree Celsius. In an embodiment, the purified mineral may further be subjected to putta system of incineration. In another embodiment, the incinerated mineral is further triturated with juice of *Aloe vera* and incinerated again to obtain a powder or Bhasma.

Example 5: Preparation of Muktashukti Bhasma

Pearl oyster shells of *Pinctada vulgaris* were collected and authenticated. The collected genuine pearl oysters were washed in potable water and dried under sun. They were pounded in a mortar and pestle into small pieces. These pieces were again washed with hot water to remove any dirt. The pieces of Muktashukti were placed in a clean cloth tied into a Pottali (bolus). That Pottali was suspended with the help of stick and immersed in Kanji present in the earthen pot such that the bottom of pottali does not touch the pots inner surface. This was kept over mild fire (65 to 80° C.) and heated for 3 hours. Kanji was added subsequently to maintain the level of Kanji during the heating procedure. pH of Kanji was recorded at every half an hour interval. After 3 hours Pottali was taken out and allowed to cool. After cooling, purified Muktashukti was collected from Pottali and washed with warm water and allowed for complete drying. Purified Muktashukti pieces were subjected to heat using Gaja puta. After self-cooling (cooling by itself, without any external aid), earthen saucer capsule was carefully collected, seal was removed, saucers separated and the material inside was collected. Content inside earthen saucer capsule was powdered and levigated with fresh juice of *Aloe vera* and prepared into discs of 0.5 cm×2.5 cm and dried under sun/hot air oven a 50° C. These dried discs were sealed in earthen saucers (1-2 layers) to form a capsule. This capsule was again subjected to heat in Gaja Puta. This procedure of levigation and incineration was repeated two times until a very fine Muktashukti Bhasma was formed.

Yashada Bhasma:

Yashada bhasma may be prepared by methods generally known in the field. The mineral or starting material used in the preparation of bhasma in the various embodiments herein includes Zinc. The starting material is further purified, triturated and incinerated to obtain Yashada Bhasma. In an embodiment, the process of preparation of Yashada bhasma includes cleaning and drying the mineral, purifying said mineral, mixing of mineral with purified mercury (also referred to as Shuddha Parada), triturating, and incinerating by putta system to obtain a powder or bhasma. In an embodiment, said purification of the mineral includes melting the mineral, and pouring in lime water. The process of purification may be repeated seven times to obtain purified mineral. In an embodiment, said mixing of mineral with purified mineral further includes melting purified mineral and adding equal quantity of Shuddha Parada. In another embodiment, the mixture of mineral and Shuddha Parada is triturated to obtain an Amalgam. The obtained Amalgam is further washed with lemon juice and added to equal quantity of purified Sulphur. In an embodiment, the mixture is further triturated to obtain a black powder. The obtained powder is then subjected to the putta system of incineration by generally known methods. The powder obtained after incineration is subjected to grinding for use as Yashda Bhasma.

Example 6: Preparation of Yashada Bhasma 99.9% pure zinc bars certified for purity by ICP-OES were collected. In samanya shodhan, the raw Yashada (zinc) was heated until it melted and then quenched sequentially in sesame oil, buttermilk, cow's urine, kanji, kullatha kwatha (7 times in each). In vishesha shodhana, the Yashada obtained in samanya shodhan was melted and quenched in lime water, followed by washing in hot water and then dried. This procedure was repeated seven times, each time using fresh batch of lime water. The shodhita (Purified) Yashada was taken in a mortar, along with equal quantity (by weight) of purified mercury and triturated to obtain an amalgam. This amalgam was washed with lemon juice and then mixed with Shodhita Gandhaka (purified Sulphur prepared as per generally known ayurvedic process) and triturated until a black, lusterless, fine powder was obtained. The black powder obtained was spread as a layer in an earthen saucer (Sharava). It was closed with another earthen saucer. Joint between the earthen saucers was sealed with mud plasters and dried to get a capsule (Sharava samputa). The incineration with traditional method of heating was carried out using kukkuta puta, the [pit of 45 cm (1×b×h)] and 60 cow dung cakes. This process was repeated four times. After complete incineration the pale yellow colored Yashada Bhasma was obtained.

Rajata Bhasma:

Rajata bhasma may be prepared by methods generally known in the field. The mineral or starting material used in the preparation of bhasma in the various embodiments herein includes Silver foil. The starting material is further purified, triturated and incinerated to obtain Rajata Bhasma.

In an embodiment, the process of preparation of Rajata bhasma includes cleaning and drying the mineral, purifying said mineral, mixing of mineral with black sulphide of mercury (also referred to as Kajjali), drying in capsules of earthern saucers, subjecting to heat, triturating, and incinerating by putta system to obtain a powder or bhasma. The trituration and incineration process of the obtained powder may further be repeated in many cycles to obtain Rajata Bhasma. In an embodiment, said purification of the mineral includes quenching the mineral in lemon juice. The process of purification may be repeated seven times to obtain purified mineral. In an embodiment, said mixing of purified mineral with Kajjali further includes mixing or applying a paste of Kajjali and lemon juice. The mineral is further dried in capsules of earthern saucers by subjected to a specific quantum and pattern of heat. The capsule is further opened upon cooling. The discs obtained from the saucers are then powdered and triturated. In an embodiment, the obtained powder is triturated in lemon juice. In another embodiment, the obtained powder is triturated in a herbal juice. The herbal juice used in the preparation of Rajata bhasma includes juice of at least one of the following herbs: *Centella asiatica, Bacopa monnieri, Convolvulus pluricaulis* and *Clitoria ternatea*. Table 8 is a list illustrating the herbs required for trituration in preparation of Rajata Bhasma.

TABLE 8

| Herbal juice used in trituration while preparing Rajata Bhasma includes the following: Juice of following herbs: | | |
| --- | --- | --- |
| 1. Mandookapami fresh leaves | *Centella asiatica* | 1 part |
| 2. Brahmi fresh plant | *Bacopa monnieri* | 1 part |
| 3. Shankhapushpi fresh plant | *Convolvulus pluricaulis* | 1 part |
| 4. Aparajita fresh plant | *Clitoria ternatea* | 1 part |

The triturated mix is then incinerated by putta system to obtain a powder. In an embodiment, the trituration and incineration process may be repeated in 8 cycles until Rajata Bhasma is obtained.

Example 7: Preparation of Rajata Bhasma 99.9% pure silver foils were procured, and purity was checked by Scanning Electron Microscope/Energy Dispersive X-ray spectroscopy analysis. The raw material was heated till red hot and quenched subsequently in Kanji, Takra, Kulattha Kwatha, Gomutra and Tila Taila, 3 times in each, for Samanya Shodhana. After every Nirvapa (heating and quenching), the liquid medium was changed.

Silver foils were again heated till red hot and quenched in lemon juice; process was repeated seven times. Lemon juice was changed after every round of quenching. Finally, Shuddha Rajata (purified silver) was collected carefully. Kajjali was prepared by mixing equal quantities of purified Parada (Mercury) and purified Gandhaka (Sulphur) and triturating until a lusterless, very fine, dark black powder was obtained. Kajjali was levigated with fresh juice of *Aloe vera* to get a smooth paste which was applied on either side of purified silver foil and dried in room temperature. These foils were spread into a layer in an earthen saucer. It was closed with another similar earthen saucer placed inverted; joint was sealed with mud plasters and dried. This earthen saucer capsule was then subjected to a specific quantum of heat in a pit using 20 cow dung cakes. After self-cooling the capsule was taken out, incinerated silver foils were carefully collected and powdered in a mortar. It was mixed with lemon juice and levigated to get a smooth paste. This paste was made into pellets of 0.5 cm thickness and 2.5 cm diameter and then dried under Sun or in hot air oven at 50° C. Dried earthen capsules containing the discs was subjected to heat using Gaja Puta. After self-cooling (cooling by itself, without any external aid), earthen saucer capsule was carefully collected, seal was removed, saucers separated and the material inside was collected. Content inside earthen saucer capsule was powdered and levigated with the liquids mentioned in Table 8 and the cycle of incineration was repeated till Bhasma was obtained (Minimum 8 times).

Shringa Bhasma:

Shringa bhasma may be prepared by methods generally known in the field. The mineral or starting material used in the preparation of Shringa bhasma in the various embodiments herein is Hart's horn. The starting material is further purified, triturated and incinerated to obtain Shringa Bhasma. In an embodiment, the process of preparation of Shringa bhasma includes cleaning and drying the mineral, purifying said mineral, triturating, and incinerating by putta system to obtain a powder or bhasma. The obtained powder is subjected to the putta system of incineration by generally known methods. The trituration and incineration process of the obtained powder may further be repeated in many cycles to obtain Shringa Bhasma. In an embodiment, the obtained powder is triturated and incinerated in 3 cycles in order to obtain Shringa Bhasma. In an embodiment, said purification of the mineral includes burning said mineral directly in flame. The mineral may be cut into small pieces and burnt directly on cow dung fire. The purified mineral may further be powdered and triturated. In an embodiment, the purified and powdered mineral is triturated with latex of *Calotropis procera* plant. The triturated mineral is then subjected to putta system of incineration by generally known methods. The powder obtained after incineration is subjected used as Shringa Bhasma.

Example 8: Preparation of Shringa Bhasma

Hart's horn was collected from authentic source. It was cut into small pieces of about 1-2 inches and directly subjected to firewood flame. Once burnt and completely blackened, it was taken out of fire and cooled. Surface of the raw material was cleaned by wiping with a clean cotton cloth. Fragile burnt pieces of Mriga Shringa were powdered in a mortar and mixed with latex of *Calotropis procera* plant. Trituration was done until a smooth paste was obtained. This paste was prepared into discs of 0.5 cm×2.5 cm and dried under sun/hot air oven 50 degrees Celsius. These dried discs were sealed in earthen saucers (1-2 layers) to form a capsule. This capsule is subjected to heat using Gaja Puta. After self-cooling (cooling by itself, without any external aid), earthen saucer capsule was carefully collected, seal was removed, saucers separated and the material inside was collected. This procedure of levigation and incineration was repeated three times until a very fine Shringa Bhasma was formed.

Shankha Bhasma:

Shankha bhasma may be prepared by methods generally known in the field. The mineral or starting material used in the preparation of Shankha bhasma in the various embodiments herein is Conch shell. The starting material is purified, triturated and incinerated to obtain Shankha Bhasma. In an embodiment, the process of preparation of Shankha bhasma includes cleaning and drying the mineral, purifying said mineral, triturating, and incinerating by putta system to obtain a powder or bhasma. The mineral is subjected to the putta system of incineration by generally known methods. The trituration and incineration process of the obtained powder may further be repeated in many cycles to obtain Bhasma. In an embodiment, said purification of the mineral is performed by Svedhana in Citrus lemon juice for six hours. In an embodiment, Svedana is a process involving wrapping the mineral in a clean cloth into a bundle, suspending the bundle through a thread from an iron rod in Citrus lemon juice taken in an earthen pot and heating. In an embodiment, said heating is performed at a controlled temperature of about 60 degree to 80 degree Celsius for a period of about 6 hours. Upon purification, the mineral is dried in capsules of earthern saucers by subjecting to a specific quantum and pattern of heat. The capsule is opened upon cooling and the discs obtained from the saucers are powdered. The obtained powder is then subjected to trituration. In an embodiment, the obtained powder is triturated in *Aloe vera* juice. The triturated mineral is incinerated by putta system to obtain a powder or Shankha Bhasma.

Example 9: Preparation of Shanka Bhasma

The outer covering (Conch shell) of shelled marine organism (family Gastropoda, Class Mollusca) was collected from known authentic source. Shankha was broken into small pieces and it was tied into a bolus with the help of two folded cloth. It was then made to hang on a stick placed across a pot which was filled with nimbu swarasam (fresh juice of Citrus limonum). This was subjected to heat for 3 hrs. at 70-80° C. After 3 hrs., it was taken out and washed in warm water and dried. purified Shankha pieces were sealed in earthen saucer capsule and subjected to heat using Gaja Puta. After self-cooling (cooling by itself, without any external aid), earthen saucer capsule was carefully collected, seal was removed, saucers separated and the material inside was collected. Content inside earthen saucer capsule was powdered and levigated with fresh juice of *Aloe vera* and prepared into discs of 0.5 cm×2.5 cm and dried under sun/hot air oven at 50 degrees Celsius. These dried discs were sealed in earthen saucers (1-2 layers) to form a capsule. This capsule was again subjected to heat in Gaja Puta. This procedure of levigation and incineration was repeated three times until a very fine Shankha Bhasma was formed.

Swarna Makshika Bhasma:

Swarna makshika bhasma may be prepared by methods generally known in the field. The mineral or starting material used in the preparation of Swarna makshika bhasma in the various embodiments herein include Copper pyrite, (also referred to as "Swarna makshika"). The starting material is purified, triturated and incinerated to obtain a Bhasma. In an embodiment, the process of preparation of Swarna makshika bhasma includes cleaning and drying the mineral, purifying said mineral, triturating with herbal decoction and/or herbal juices, and incinerating by putta system to obtain a powder or bhasma. The obtained powder is subjected to the putta system of incineration by generally known methods. The trituration and incineration process of the obtained powder may further be repeated in many cycles to obtain Swarna makshika Bhasma. In an embodiment, the obtained powder is triturated and incinerated for 10 cycles in order to obtain Swarna makshika Bhasma. In an embodiment, said purification process of the mineral includes mixing the mineral with rock salt and lemon juice, and heating. In an embodiment, said heating is performed in an open pan until the mixture is partially oxidized and turns into a reddish colored powder. The herbal decoction/juice used in the trituration process of Swarna makshika bhasma includes a decoction of at least one of the following ingredients: *Emblica officinalis, Terminalia chebula, Terminalia bellerica, Cyperus rotundus, Ficus benghalensis, Curcuma longa* and *Rubia cordifolia*. Table 9 depicts the ingredients of the herbal decoction used in the preparation of Swarna makshika bhasma.

TABLE 9

Ingredients for Herbal decoction used for trituration while preparing Swarna makshika Bhasma.
Decoction of following herbs:

| | | | |
|---|---|---|---|
| 1 | Amalaki dried fruit | *Emblica officinalis* | 1 part |
| 2 | Hareetaki dried fruit | *Terminalia chebula* | 1 part |
| 3 | Vibheetaki dried fruit | *Terminalia bellerica* | 1 part |
| 4 | Musta dried rhizome | *Cyperus rotundas* | 1 part |
| 5 | Vata dried root bark | *Ficus benghalensis* | 1 part |
| 6 | Haridra dried rhizome | *Curcuma longa* | 1 part |
| 7 | Manjishtha dried root | *Rubia cordifolia* | 1 part |
| 8 | Jala | Water | 112 parts |
| | Avashesha (Reduced to) | | 1/8 part of liquid |

Example 10: Preparation of Swarna Makshika Bhasma

The raw material used was Swarna Makshika i.e. Copper pyrite. [Copper pyrite which looks yellow with iridescent tarnish having greenish black streak, uneven fracture, metallic luster, brittle tenacity, opaque with hardness between 3 and 4, specific gravity between 3.4 and 3.7 was selected. A sample of Swarna Makshika with, Copper: not <5%, Iron: not <20%, Sulphur: not <12% was selected.]. Sample was washed with demineralized water to remove dirt and dried in hot air oven at 50° C. The raw material was then subjected to purification (Shodhana), wherein at first the Swarna makshika was powdered in an iron mortar with an iron pestle. A clean and dry iron pan was then heated on a charcoal furnace onto which the powdered Swarna makshika and Saindhava Lavana (Rock salt) $1/3^{rd}$ of Swarna Makshika were placed. This mixture was subjected to intense heat with frequent addition of lemon juice until the liberation of sulfur fume stopped and it turned red. The process was completed in 3 days and the final product called Shodhita Swarna makshika was obtained. This powder was mixed well with water, then water was decanted to remove excess of salt. It was then dried under sun or in hot air oven at 50° C. to get powder.

The purified Swarna Makshika powder was triturated with a herbal decoction provided in Table 9 and/or lemon juice for about six hours until a soft homogenous paste was obtained. The dough obtained was prepared into discs of 0.5 cm thickness and 2.5 cm diameter. Discs were dried under Sun or/in hot air oven at 50° C. Dried discs were spread as a layer in an earthen saucer (Sharava). It was closed with another earthen saucer. The joint between the earthen saucers is sealed with mud plasters and dried to get a capsule (Sharava samputa). The dried earthen capsule containing the discs is subjected to heat using Gaja Puta. After self-cooling (cooling by itself, without any external aid), earthen saucer capsule was carefully collected, seal was removed, saucers separated and the material inside was collected. Swarna Makshika discs were powdered and levigated with lemon juice. Then prepared into discs, dried, encapsulated and subjected to heat again. This cycle of grinding with lemon juice and heating was repeated at least 10 times or until Bhasma was properly prepared which was ascertained by specific tests that are generally known in the field.

Pravala Bhasma:

Pravala bhasma may be prepared by methods generally known in the field. The mineral or starting material used in the preparation of Pravala bhasma in the various embodiments herein is Coral. The starting material is purified, triturated and incinerated to obtain Pravala Bhasma. In an embodiment, the process of preparation of Pravala bhasma includes cleaning and drying the mineral, purifying said mineral, triturating, and incinerating by putta system to obtain a powder or bhasma. The mineral is subjected to the putta system of incineration by generally known methods. The trituration and incineration process of the obtained powder may further be repeated in many cycles to obtain Bhasma. In an embodiment, said purification of the mineral is performed by boiling the mineral in an alkaline solution of Barilla (also known as Sarja Kshara). In an embodiment, boiling is performed at a temperature of about 65 to 80 degree Celsius for about 3 hours. Upon purification, the mineral is sealed in capsules of earthern saucers ad dried by subjecting to a specific quantum and pattern of heat. The capsule is opened upon cooling and the discs obtained from the saucers are powdered. The obtained powder is then subjected to trituration. In an embodiment, the obtained powder is triturated with herbal juice and cow's milk. The herbal juice used in the preparation of Pravala Bhasma includes juice of at least one of the following herbs: *Aloe vera, Asparagus racemosus* and Rose water. Table 10 depicts the ingredients used in trituration while preparing Pravala Bhasma.

TABLE 10

Ingredients used in trituration while preparing Pravala Bhasma includes the following:
Juice of following:

| | | | |
|---|---|---|---|
| 1. | Kumari fresh leaves | *Aloe vera* | 1 part |
| 2. | Shatavari fresh root | *Asparagus racemosus* | 1 part |
| 3. | Taruni Parisruta Jala | Rose water | 1 part |
| 4. | Godugdha | Cow milk | 1 part |

The triturated mineral is then incinerated by putta system to obtain a powder. In an embodiment, the trituration and incineration process may be repeated in 4 cycles until Pravala Bhasma is obtained.

Example 11: Preparation of Pravala Bhasma

Good quality coral was collected from known source and authenticated with the help of mineralogical tools. Pieces of coral were washed in demineralized water, dried in hot air oven at 50° C., wrapped by a clean, starch less cloth and tied into a bolus. This bolus was suspended with the help of a thread from an iron rod placed at the inlet of an earthen pot. Inside the pot Sarja Kshara (Barilla) dissolved in water was taken. Height of the bolus was maintained in such a way that it does not touch the base of the pot but remains immersed in the liquid throughout the procedure. Pot was heated at a temperature between 65 to 80° C. for three hours. Then the cloth bolus was opened, purified coral was removed, washed with hot water and dried. Purified coral pieces were sealed in earthen saucer capsule and subjected to heating in Gaja Puta. After self-cooling (cooling by itself, without any external aid), earthen saucer capsule was carefully collected, seal was removed, saucers separated and the material inside was collected. Content inside earthen saucer capsule was powdered and levigated with specified juice for about six hours until a soft homogenous paste was obtained. The dough obtained was prepared into discs of 0.5 cm thickness and 2.5 cm diameter. Discs were dried under Sun or/in hot air oven at 50° C. The dried discs were spread as a layer in an earthen saucer (Sharava). It was closed with another earthen saucer. Joint between the earthen saucers was sealed with mud plasters and dried to get a capsule (Sharava samputa). Dried earthen capsule containing the discs was subjected to heat using Gaja Puta. This procedure was repeated four times using different juice mentioned in Table 10 each time for levigation. After 4 such cycles of incineration Pravala Bhasma was formed.

Adding Powdered Herbs into Said Grinder and Grinding:

In the various embodiments disclosed herein, the step of adding of herbs includes adding herbs to the levigated mixture and grinding with a second portion of the grinding decoction, to obtain a homogenous mixture. In an embodiment, said grinding is performed in a grinder such that a homogenous mass is obtained. The herbs that are mixed with the levigated mixture include finely powdered herbs that are instrumental in the composition as disclosed in the various embodiments herein. In an embodiment, said herbs includes whole plant of *Bacopa monnieri* and *Convolvulus pluricaulis*; seeds of *Mucuna pruriens*; rhizome of *Nardostachys jatamansi*; roots of *Rauwolfia serpentina*, *Withania somnifera*, *Sida cordifolia* and *Acorus calamus*; and fruits of *Emblica officinalis*.

In another embodiment, said herbs further include at least one herb selected from a group consisting of dried and finely powdered seeds of *Elettaria cardamomum*; roots of *Picrorhiza kurroa*, *Plumbago zeylanica*, *Rubia cordifolia*, *Hemidesmus indicus*, *Vetiveria zizanioides*, *Alpinia galangal*, *Glycyrrhiza glabra* and *Inula racemosa*; fruits of *Terminalia chebula*, *Terminalia bellerica*, *Piper nigrum* and *Piper longum*; heartwood of *Santalum album* and *Pterocarpus santalinus*; rhizome of *Zingiber officinale* and *Curcuma longa*; bark of *Cinnamomum zeylanica*; floral bud of *Syzygium aromaticum*; leaves of *Ocimum sanctum*, stem of *Tinospora cordifolia*; bark of *Cassia fistula*; fruit of *Embelia ribes*; heartwood of *Prunus cerasoides*; leaves of *Ricinus communis*; roots of *Boerhavia diffusa*; stem bark of *Terminalia arjuna*; and stamen of *Mesua ferrea*. In an embodiment, finely powdered herbs may be obtained by powdering and sieving the dry herb or herb components through 80 mesh screen. In the various embodiments disclosed herein, grinding may be performed by methods generally known in the field. In an embodiment, grinding is performed in a grinder at about 120 rpm to obtain an herbal mixture.

In an embodiment, the grinding decoction is added, subsequent to the addition of powdered herbs, in small quantities at frequent intervals. Once the grinding decoction is added grinding is continued for 65-75 hours at about 100-120 rpm. In an embodiment, grinding is continued for 72 hours at about 120 rpm, to obtain a homogenous mass. In an embodiment, the method of preparation further includes adding excipient to the homogenous mass, wherein *gum acacia* is added by dissolving in a third portion of grinding decoction. Grinding may further be continued once the excipient is added for a period of 1 to 4 hours to obtain a semisolid mass. In an embodiment, grinding is continued for a period of 3 hours.

Example 12: Preparation of the Composition

Quality approved raw materials were cleaned and thoroughly washed with potable demineralized water and drying in hot air oven at 50 degrees Celsius. Washed raw materials were spread over clean dry trays and dried in hot air oven until moisture content was minimum and within the prescribed limits.

Ingredients mentioned in Table 3 were coarsely powdered and sieved with size 10 mesh. Powdered ingredients were uniformly mixed. The coarse powder of ingredients was mixed with potable water such that the quantity of water was 16 times as that of the powdered ingredients. The mixture was kept soaked overnight. It was then heated at a temperature between 80 to 85° C. until the quantity of the liquid was reduced to ⅛th of the initial volume, concentration was confirmed with the help of Brix meter. The decoction was then filtered to separate the debris. Guggulu and Shilajit were dissolved in small amount of hot decoction and added to a grinder. This was followed by the addition of thoroughly mixed Bhasma ingredients. The mixture was levigated with some amount of decoction for 3 hours. Herbs (i.e. whole plant of *Bacopa monnieri* and *Convolvulus pluricaulis*; seeds of *Mucuna pruriens*; rhizome of *Nardostachys jatamansi*; roots of *Rauwolfia serpentina*, *Withania somnifera*, *Sida cordifolia* and *Acorus calamus*; and fruits of *Emblica officinalis*; seeds of *Elettaria cardamomum*; roots of *Picrorhiza kurroa*, *Plumbago zeylanica*, *Rubia cordifolia*, *Hemidesmus indicus*, *Vetiveria zizanioides*, *Alpinia galangal*, *Glycyrrhiza glabra* and *Inula racemosa*; fruits of *Terminalia chebula*, *Terminalia bellerica*, *Piper nigrum* and *Piper longum*; heartwood of *Santalum album* and *Pterocarpus santalinus*; rhizome of *Zingiber officinale* and *Curcuma longa*; bark of *Cinnamomum zeylanica*; floral bud of *Syzygium aromaticum*; leaves of *Ocimum sanctum*, stem of *Tinospora cordifolia*; bark of *Cassia fistula*; fruit of *Embelia ribes*; heartwood of *Prunus cerasoides*; leaves of *Ricinus communis*; roots of *Boerhavia diffusa*; stem bark of *Terminalia arjuna*; and stamen of *Mesua ferrea*.) were finely powdered and sieved with sieve size 80 mesh screen and mixed. This powder was added to the grinder along with the grinding decoction. Grinding decoction was added little by little while grinding, at frequent intervals, to obtain a homogenous mass. Grinding was performed at 120 rpm for 72 hours. Gum was dissolved in a portion of the grinding decoction and added to the homogenous mass. Further grinding was done for three hours to obtain a semisolid mass which was dried in hot air oven at 50 degrees Celsius. The dried mass was granulated and punched in multistation tablet press to get 500 mg tablets.

Treatment

Disclosed herein are embodiments of a method for the treatment and management of Cognitive dysfunction. Further disclosed are embodiment of the method for the treatment and management of Dementia. Also disclosed is a method of boosting memory in children. Further disclosed are embodiments of a method of improving or restoring memory of an individual having reduced or low memory power. Further embodiments herein are also instrumental in the treatment and management of neuro-degenerative diseases and associated symptoms. Accordingly, embodiments of a method for treatment and management of neuro-degenerative diseases and associated symptoms are also provided herein. The symptoms of neuro-degenerative diseases include the generally known symptoms such as apathy, anxiety, memory loss, speech changes, etc. Neuro-degenerative diseases according to the various embodiments herein include generally known neuro-degenerative diseases such as Parkinson's disease, Alzheimer's disease, dementia, etc.

In an embodiment, the method includes administering to a patient a composition as described in the embodiments disclosed herein. The term "patient" according to the various embodiments herein includes any individual in need thereof including, but not limited to, individuals intending to improve or restore cognitive function; individuals having neuro-degenerative diseases such as Parkinson's disease, Alzheimer's disease and dementia; individuals having low memory power; individuals having symptoms of neuro-degenerative diseases such as apathy, anxiety, memory loss, speech changes, etc; individuals having dementia; children intending to improving memory, etc. Further disclosed are embodiments of a method for manufacturing a medicament. In an embodiment, the method for manufacturing a medicament comprises combining a suitable excipient and the disclosed composition. In an embodiment, the composition is present in an amount effective for treatment of Dementia.

In an embodiment, the method includes administering to a patient a composition having *Bacopa monnieri* (4 to 8 wt. %), *Convolvulus pluricaulis* (2 to 4 wt. %), *Mucuna pruriens* (2 to 4 wt. %), *Nardostachys jatamansi* (2 to 4 wt. %), *Rauwolfia serpentina* (2 to 4 wt. %), *Withania somnifera* (3 to 7 wt. %), *Acorus calamus* (2 to 4 wt. %), *Sida cordifolia* (2 to 4 wt. %), *Emblica officinalis* (3 to 7 wt. %), *Santalum album* (≤2 wt. %), *Pterocarpus santalinus* (≤2 wt. %), *Glycyrrhiza glabra* (≤2 wt. %), *Terminalia chebula* (≤2 wt. %), *Terminalia bellerica* (≤2 wt. %), *Zingiber officinale* (≤2 wt. %), *Piper nigrum* (≤2 wt. %), *Piper longum* (≤2 wt. %), *Curcuma longa* (≤2 wt. %), *Inula racemosa* (≤2 wt. %), *Cinnamomum zeylanica* (≤2 wt. %), *Elettaria cardamomum* (≤2 wt. %), *Syzygium aromaticum* (≤2 wt. %), *Ocimum sanctum* (≤2 wt. %), *Tinospora cordifolia* (1 to 3 wt. %), *Hemidesmus indicus* (≤2 wt. %), *Vetiveria zizanioides* (≤2 wt. %), *Alpinia galangal* (1 to 3 wt. %), *Cassia fistula* (1 to 3 wt. %), *Embelia ribes* (≤2 wt. %), *Prunus cerasoides* (≤2 wt. %), *Rubia cordifolia* (≤2 wt. %), *Ricinus communis* (≤2 wt. %), *Boerhavia diffusa* (≤2 wt. %), *Terminalia arjuna* (≤2 wt. %), *Commiphora mukul* (≤2 wt. %), *Picrorhiza kurroa* (≤2 wt. %), *Plumbago zeylanica* (≤2 wt. %), *Mesua ferrea* (≤2 wt. %), Rasa sindura (≤2 wt. %), Shilajit (≤2 wt. %), Swarna makshika bhasma (≤2 wt. %), Loha Bhasma (≤2 wt. %), Abhraka bhasma (≤2 wt. %), Rajata Bhasma (≤2 wt. %), Muktashukti Bhasma (≤2 wt. %), Pravala Bhasma (≤2 wt. %), Shringa Bhasma (≤2 wt. %), Vanga Bhasma (≤2 wt. %), Yashada Bhasma (≤2 wt. %), Shankha Bhasma (≤2 wt. %), Mandura Bhasma (≤2 wt. %), and a suitable excipient.

The disclosed method of treatment may be used as a primary line of treatment or as an adjunct to other treatment methods for Cognitive dysfunction and dementia.

The patient may be administered a therapeutically effective amount of the disclosed composition. The therapeutically effective amount may vary depending on the patient. In an embodiment, the therapeutically effective amount is 500 to 1000 mg administered one to three times a day. The dosages for children would vary. The composition as disclosed in Table 1 (also referred as Test item or Test drug or Muniprajnaa) was subjected to toxicity and efficacy studies, results of which are provided herein.

Toxicity Study

Test drug was administered once orally to overnight fasted female Wistar rats at 2000 and 5000 mg/kg body weight (2 steps/dose; 3 animals/step) at a dose volume 10 ml/kg. Body weight was recorded on day 0, 7 and 14. Mortality/Clinical signs were observed at approximately 30 minutes, 1, 2 and 4 h on day 0 (after test item administration) and thereafter once daily for 14 days.

All the experimental animals showed gain in body weight on day 7 and 14 in comparison to their day 0 body weight. No clinical signs and mortality were observed for 14 days in all experimental animals No gross lesions were detected in animal treated with 2000 mg/kg body weight, whereas in animal number 8, treated with 5000 mg/kg body weight shows multifocal point of congestion in lungs. No gross lesions were detected in all other organs of experimental animals treated with 5000 mg/kg body weight.

Histopathologic examination of lungs of animal number 8 revealed alveolar hemorrhages, alveolar thickening with mononuclear cells infiltration and multifocal aggregates of mixed population of inflammatory cells around blood vessels and bronchioles.

Based on the above observations, the LD50 value of "Test drug" was found to be greater than 5000 mg/kg body weight and classified as Category-5 or unclassified based on Globally Harmonised Classification System (GHS) for Chemical Substances and Mixtures.

Efficacy Study 1: Evaluation of Efficacy of Test Drug Using MPTP (1 methyl 4 1-methyl-4-phenyl-1,2,3,6-tetrahydropyridine) Induced Parkinson Disease Mice Model.

Following parameters were considered:

Beam Walk Test:

Time taken to cross the beam to reach enclosed escape platform, number of foot slips and immobility period were recorded Immobility period and number of foot slips were less in test drug treated group when compared to MPTP group. Result was dose dependent and comparable to the standard drug R-Deprenyl.

Open Field Test:

Number of lines crossed, Number of center squares entered, and Number of rearing were better in test drug treated group when compared to MPTP group. Duration of center square entries was less in test drug treated group when compared to MPTP group. The result was dose dependent and comparable to the standard drug R-Deprenyl.

The above results indicated that test drug tablet has a promising anti Parkinson activity.

Efficacy Study 2: Evaluation of Efficacy of Test Drug Tablets in Scopolamine Induced Memory Impairment in Male Swiss Albino Mice.

Summary: In this study, the anti-amnesic activity of test drug tablets was tested by using acute models of Alzheimer's viz., scopolamine induced memory impairment in mice using Passive avoidance test and Novel object recognition test. Test drug tablets (800 mg/kg) significantly ($P<0.001$) and ($P<0.01$) decreased the time spent by animals in the dark compartment and number of crossings respectively in the Passive avoidance test. However, it did not affect the latency time to enter dark compartment in this model. The activity was comparable to the standard drug Donepezil (5 mg/kg) which significantly ($P<0.01$) increased the latency time to enter the dark compartment and the total time spent in the dark compartment. Similarly, test drug tablets (800 mg/kg) significantly ($P<0.05$) and ($P<0.01$) improved the discrimination and recognition index scores respectively in Novel object recognition test. These results were comparable to the standard drug Donepezil (5 mg/kg) (manufactured by: EISAI PHARMA) which significantly ($P<0.01$) improved the discrimination and recognition indices. This was in correlation with the reduced glutathione activity, where test drug (400 & 800 mg/kg) showed significant ($P<0.0001$) elevation of reduced glutathione levels. (Reference citation: Kanwal, A. et al. (2010) '*Anti-Amnesic Activity of Vitex Negundo in Scopolamine Induced Amnesia in Rats*', *Pharmacology & Pharmacy*, 01(01), pp. 1-8.)

I. Passive Avoidance Test:

Procedure:

The apparatus consists of two compartments, a rectangular larger compartment, and smaller dark compartment. The rectangular larger compartment has 50 cm×50 cm grid floor and wooden walls of 35 cm height. The box was illuminated with a 100-W bulb placed 150 cm above the center. It has a roof, which can be opened or closed. One of the walls has a 6 cm×6 cm opening which to a dark smaller compartment having dimensions of 15 cm×15 cm. This compartment is provided with an electrifiable grid, which is connected to a constant current stimulator, and a ceiling that can be opened or closed. The connection between the two compartments can be closed with a sliding door made of transparent Plexiglas. The experiment may be performed by the method of Bures J et al., with modifications. The experiment was divided into three parts: An exploration test, Learning (Electric shock), and Retention testing.

1. An Exploration Test:

The exploration test is done in three trials. During this, mice are placed in the center of the larger compartment facing away from the entrance to the dark compartment. The door between the two compartments is kept open. The mice are allowed to explore the apparatus (both larger and smaller compartments) for 3 minutes. In each trial, two things will be examined: Time taken by the mice to enter the dark compartment at each trial; and the total time spent by the animal in the dark compartment, using a stop-watch.

2. Learning (Electric Shock):

After the last exploration trial, the mice are placed in the larger compartment as done in the trial sessions. When the animal enters the dark compartment, the sliding door between the two compartments of the apparatus is closed and three strong foot shocks (50 Hz, 1.5 mA, and 1 s duration) is given at 5-second intervals. The ceiling is immediately opened, and the mice are then placed back to their home cage.

3. Retention Testing.

The retention test is done after 24 hours. The mice are placed at the center of the larger compartment facing away from the opening to the smaller compartment for a maximum time of 3 minutes. The sliding door is kept open during this period and the animal latency time required to enter the dark compartment is noted. The latency time is noted as 3 minutes for those animals that did not enter the dark compartment within the time limit of 3 minutes. The total time spent by the mice in both light and dark compartments during the memory retention trial is noted. The mice which did not enter the dark compartment indicated the positive memory retention. Table 11: depicts the treatment details for Passive Avoidance test.

TABLE 11

Passive Avoidance test.

| S. No | Treatment | Dose | No. of Animals |
|---|---|---|---|
| 1 | Vehicle Control | Sodium CMC | 6 |
| 2 | Scopolamine | 1 mg/kg | 6 |
| 3 | Donepezil | 5 mg/kg | 6 |
| 4 | test drug | 400 mg/kg | 6 |
| 5 | test drug | 800 mg/kg | 6 |
| | Total | | 30 |

II. Novel Object Recognition Test:

Animals should be acclimatized to the experimental room for one hour before starting the actual study. On day one, animal will be habituated to the experimental area for 20 mins. On day two, animals will be subjected to the familiarization trial. In familiarization trial, animals will be introduced into area having a pair of similar kind of objects. The time spent by the animal at each object is noted in secs. Recognition trial is done after the optimized inter trial interval of 24 hr. In this, the test is performed by replacing one of the familiar objects with novel object, and the time spent by the animal at each object is noted in secs. Table 12: depicts the treatment details for Novel Object Recognition test.

TABLE 12

Novel Object Recognition test

| S. No | Treatment | Dose | No. of Animals |
|---|---|---|---|
| 1 | Vehicle Control | Sodium CMC | 6 |
| 2 | Scopolamine | 1 mg/kg | 6 |
| 3 | Donepezil | 5 mg/kg | 6 |
| 4 | test drug | 400 mg/kg | 6 |
| 5 | test drug | 800 mg/kg | 6 |
| | Total | | 30 |

Parameters:

Recognition index: (B/A+B) and Discriminative index: (B−A)/(A+B)

A=time spent in sec. by mice exploring familiar object in choice trial

B=time spent by mice exploring novel object in choice trial

A+B=time in sec. spent by mice exploring familiar and novel objects in choice trial.

III. Biochemical Parameters:

Tissue Preparation and Homogenization:

All the animals were sacrificed under ether anesthesia and their brains were collected and frozen immediately in −20° C. The collected brain was used for homogenization. A 10% w/v of brain homogenate was prepared by using phosphate buffer saline pH 7.0. The homogenization was done on the ice using an ultra-homogenizer operated at 9500 rpm thrice at an interval of few seconds.

1. Estimation of Reduced Glutathione (GSH):

Principle:

GSH plays important role in preventing damage caused to the cellular compound by oxidative stress, heavy metals and lipid peroxidation. In healthy cell 90% of GSH is present in the reduced form. In reduced state thiol group is responsible for neutralization of ROS. GSH acts as a non-protein with sulfhydryl group in its structure. By sulfhydryl group of GSH, reduction of 5,5'-Dithio bis 2-nitro benzoic acid (DTNB) occurs which results in intense yellow colour. At 412 nm, the absorbance of reduced chromogen is measured. The absorbance of reduced chromogen is directly proportional to GSH in tissue.

Reagents: 5% TCA distilled water [mixed 5 g of TCA in 100 ml of distilled water]; Phosphate buffer (0.2 M), pH 8.0 [0.281 g sodium dihydrogen phosphate and 2.641 g disodium hydrogen phosphate mixed in 100 ml of distilled water; and DTNB (0.6 mM) p-H 8.0 [20 mg DTNB in 50 ml of phosphate buffer of pH 8.0].

Procedure: Reduced glutathione was estimated according to Ellman's method. 2.500 µl of brain homogenate is centrifuged with 500 µl TCA solution at 3000 rpm at 4° C. for 5 mins and the supernatant was collected. For 500 μL of supernatant, 3 ml of phosphate buffer solution and 0.5 ml of DTNB was added and incubated at 37° C. for 10 minutes. A yellow color was developed, which was measured at 412 nm using UV spectrophotometer (model: UV-1650PC; Shimadzu). Results were calculated using the molar extinction co-efficient. GSH activity was expressed as micromole per mg of protein.

2. Measurement of Lipid Peroxidation (LPO):

Principle: Oxidative damage of lipid is called as lipid peroxidation. In cell membrane, free radicles take up an electron from the lipid which results in cell damage. In LPO, a chain reaction occurs with three major steps including, initiation, propagation and termination. Poly unsaturated fatty acids are most affected in this process. From the breakdown of polyunsaturated fatty acids, malondialdehyde (MDA) is formed. For the determination of extend of LPO, MDA serves as a convenient index. In this process, MDA reacts with TBA reagent and forms red color species which is measured at 532 nm.

Reagents: TBA-TCA-HCl reagent. 15% w/v trichloro acetate (TCA) (SRL Chemicals); 0.375% w/v Thiobarbituric acid (TBA) (TCI chemicals); and 0.2 ml of 0.25N HCl were used to make a solution. For the dissolution of TBA, the solution was mildly heated; Sodium CMC (0.25% w/v in water) (Merck).

Procedure: LPO activity was measured by the method of Konings (1979). A mixture of 0.5 ml tissue homogenate, 2.5 ml of Thiobarbituric acid (TBA) and TCA reagent mixture was heated at 90° C. for 10 min. The above mixture was centrifuged at 4° C. at 2000 RPM for 5 min. At 525 nm, the absorbance of given mixture was taken by the photometric method. LPO was expressed as MDA per mg of protein.

CMC, it was then diluted to 40 mg/ml using an equal volume of 0.25% W/V CMC just prior to the administration at a dose volume of 10 ml/kg. The dose was given per orally at 800 mg/kg and 400 mg/kg, formulated in CMC. Treatment to all groups was done for 14 days once Daily before the initiation of the passive avoidance test and novel object test.

Results

Figure 2:
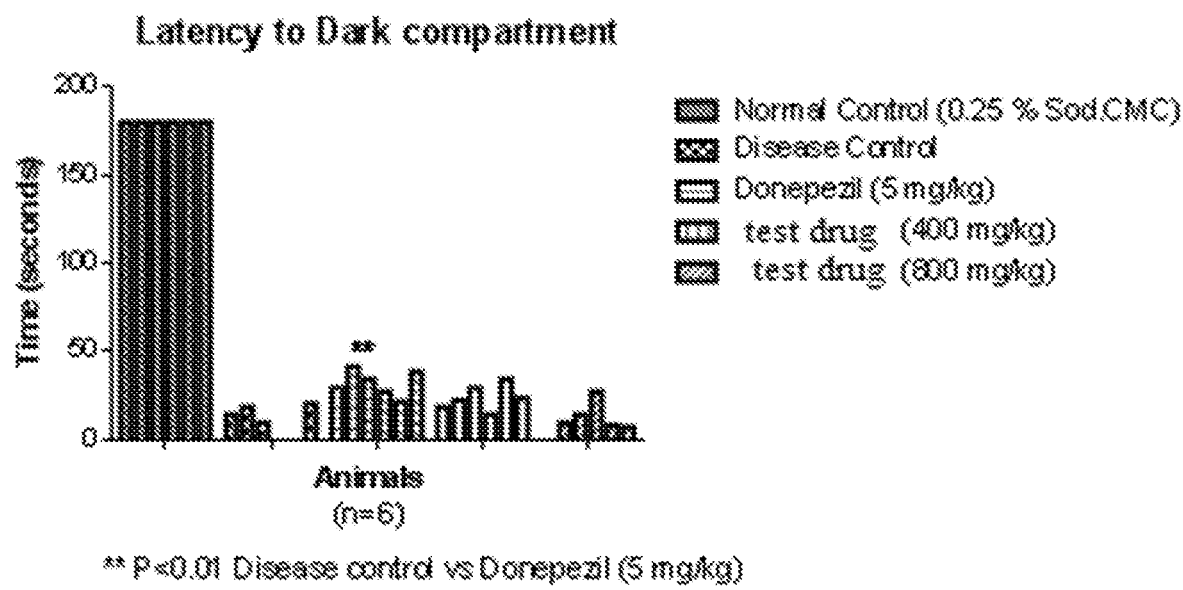
FIG. 2 is a graph depicting the results of Passive avoidance test; particularly depicting latency to Dark compartment among various treatment groups.
Figure 3:
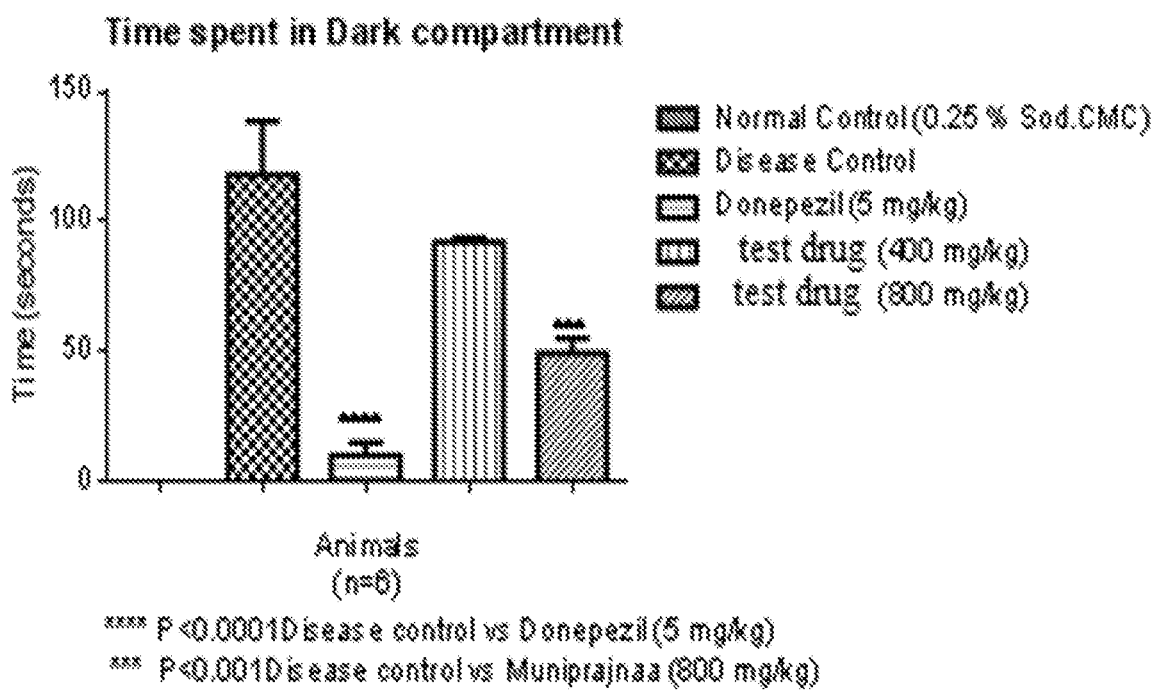
FIG. 3 is a graph depicting the results of Passive avoidance test particularly depicting the time spent by various treatment groups in Dark compartment.
Figure 4:
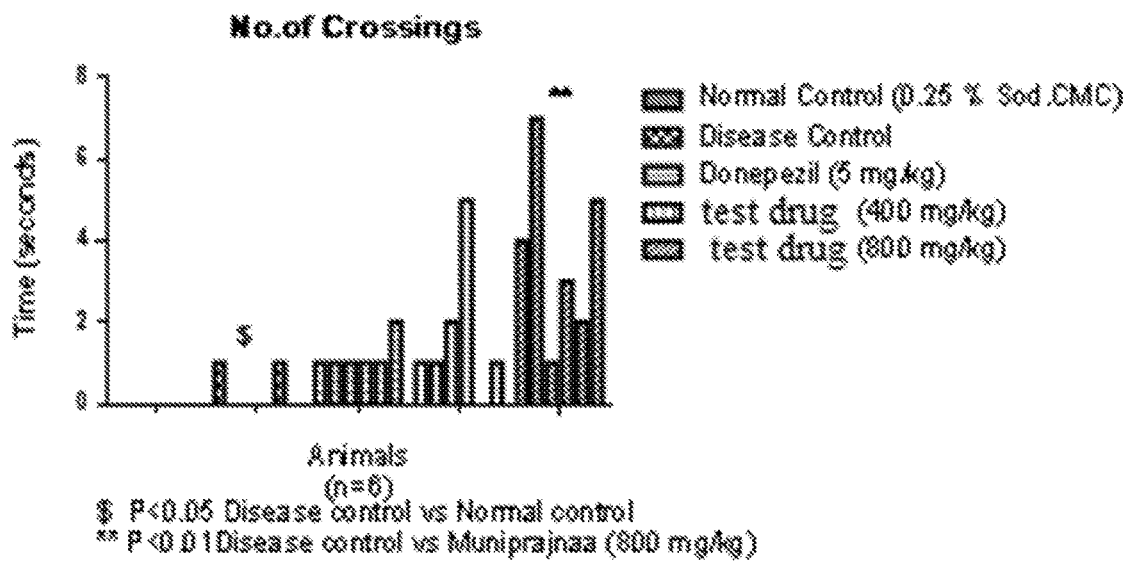
FIG. 4 is a graph depicting the results of Passive avoidance test particularly depicting the number of crossing by various treatment groups.

Passive Avoidance Test: Scopolamine (1 mg/kg, i.p.) administration has significantly impaired the memory retention ability of mice as seen in disease control group. In this group the latency time of animals to enter dark compartment and number of crossings have significantly ($P<0.0001$) reduced while the time spent by the animals in the dark compartment significantly ($P<0.0001$) increased. This indicates that administration of scopolamine has successfully induced memory impairment. Treatment with the standard drug Donepezil (5 mg/kg, p.o.) significantly ($P<0.01$) increased the latency time of the animals to enter the dark compartment and simultaneously the time spent in the dark compartment was significantly ($P<0.0001$) reduced. Test drug (800 mg/kg) significantly ($P<0.001$) reduced the time spent by the animals in the dark compartment and increased the number of crossings ($P<0.01$), whereas test drug at a dose of 400 mg/kg, p.o. did not show significant improvement in any of the parameters. Table 13 depicts the results of Passive avoidance test. FIGS. 2, 3 and 4 depict the results of the Passive avoidance test. FIG. 2 is a graph depicting the latency to Dark compartment among the test animals. FIG. 3 is a graph depicting the time spent in the Dark compartment by the test animals, wherein Muniprajnaa is the Test drug. FIG. 4 is a graph depicting the number of crossing by the test animals, wherein Muniprajnaa is the Test drug.

TABLE 13

Results of Passive avoidance test.

| Parameters | Normal Control | Disease Control | Donepezil (5 mg/kg) | Test drug (400 mg/kg) | Test drug (800 mg/kg) |
|---|---|---|---|---|---|
| Latency to Dark Compartment | 180 ± 0 | 36.83 ± 14.68 | 31.67 ± 3.03 | 23.33 ± 2.96 | 22.83 ± 10.29 |
| Time spent in dark compartment | 0 ± 0 | 95.17 ± 19.70 | 17.33 ± 8.31 | 110.67 ± 11.89 | 59.33 ± 7.45 |
| No. of crossings | 0 ± 0 | 2.17 ± 1.14 | 1.17 ± 0.17 | 1.67 ± 0.71 | 3.67 ± 0.88 |

Values indicated as MEAN ± SEM.

Statistical analysis: All values are represented as the means±SEM of six mice. One-way ANOVA using Dunnett test as a post hoc method of analysis was performed, where P values compared to scopolamine group. All the results were calculated using Excel 2016 and Graph pad prism version 6.

Test animals: Species/strain used—Swiss albino mice; Microbiological status of the animals—No microbial infection has been observed before and after the study; Number-30 male mice; Age—9-10 weeks; Weight: 20-25 g; Sex of animals—Males are suitable animals and their biochemical parameters are less affected by estrous cycle and hormonal variations, unlike female mice. Source, housing conditions, diet, etc.—as per Committee for the Purpose of Control and Supervision of Experiments on Animals (CPCSEA) guidelines.

Figure 5:
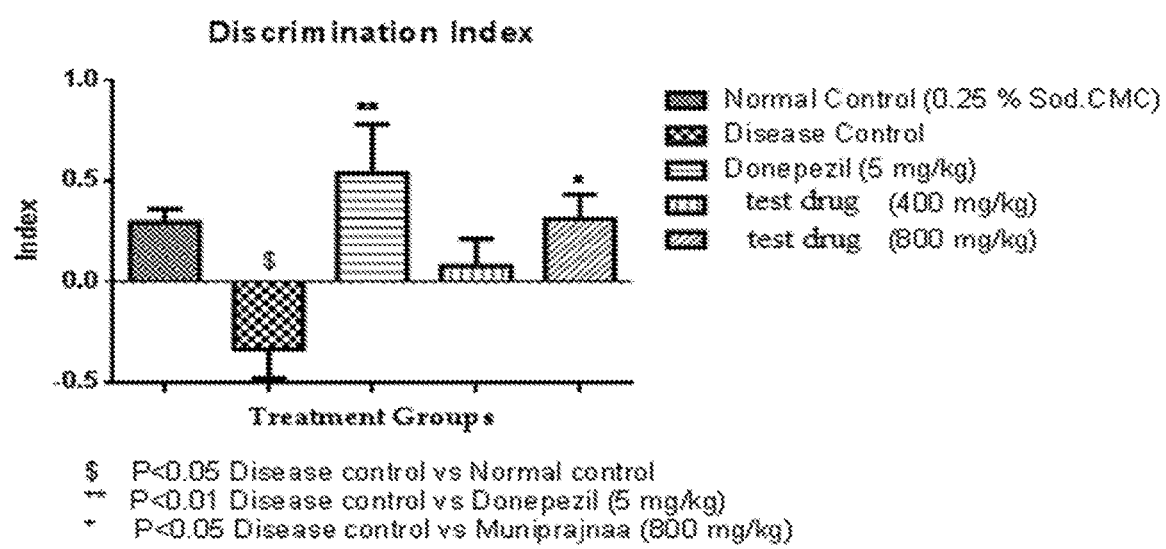
FIG. 5 is a graph depicting results of Novel Object Recognition Test (NORT); particularly Discrimination index in various treatment groups.
Figure 6:
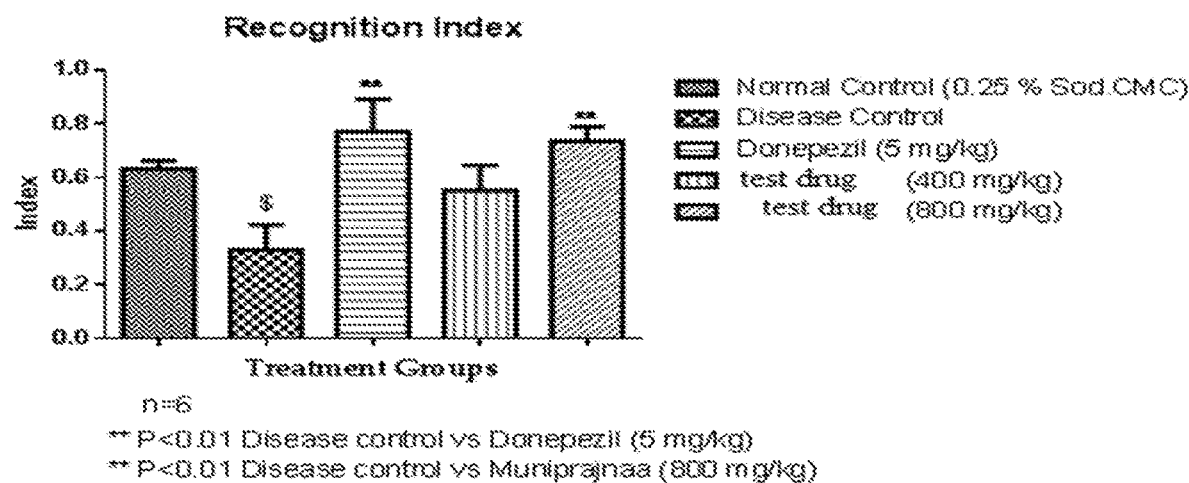
FIG. 6 is a graph depicting results of Novel Object Recognition Test (NORT); particularly depicting Recognition index in various treatment groups.

Test conditions: Test drug is brown compressed tablets. The dose stock was prepared at 80 mg/ml in 0.25% W/V Novel Object Recognition Test: Scopolamine (1 mg/kg, i.p.) administration has significantly impaired the memory retention ability of mice as seen in disease control group. The animals in this group have significantly ($P<0.05$) failed to improve the discrimination and recognition indices. Treatment with standard drug donepezil (5 mg/kg, p.o.) has significantly ($P<0.01$) improved both discrimination and recognition index. Treatment with test drug (800 mg/kg, p.o.) significantly ($P<0.05$) & ($P<0.01$) improved the discrimination and recognition indices respectively, as compared to the disease control group. Table 14 depicts the results of Novel Object Recognition Test (NORT), Discrimination index. Table 15 depicts the results of Novel Object Recognition Test (NORT), Recognition index. FIG. 5 is a graph depicting Discrimination index, wherein Muniprajnaa is the Test drug. FIG. 6 is a graph depicting Recognition index, wherein Muniprajnaa is the Test drug.

TABLE 14

Discrimination index.
NORT (Discrimination Index)

| Treatment | Normal Control | Disease Control | Donepezil (5 mg/kg) | Test drug (400 mg/kg) | Test drug (800 mg/kg) |
|---|---|---|---|---|---|
| Mean ± SEM | 0.266 ± 0.06 | −0.174 ± 0.14 | 0.025 ± 0.36 | −0.281 ± 0.24 | 0.313 ± 0.12 |

Values indicated as MEAN ± SEM.

TABLE 15

Recognition index.
NORT (Recognition Index)

| Treatment | Normal Control | Disease Control | Donepezil (5 mg/kg) | Test drug (400 mg/kg) | Test drug (800 mg/kg) |
|---|---|---|---|---|---|
| Mean ± SEM | 0.633 ± 0.03 | 0.329 ± 0.09 | 0.513 ± 0.18 | 0.276 ± 0.13 | 0.490 ± 0.16 |

Values indicated as MEAN ± SEM.

Figure 7:
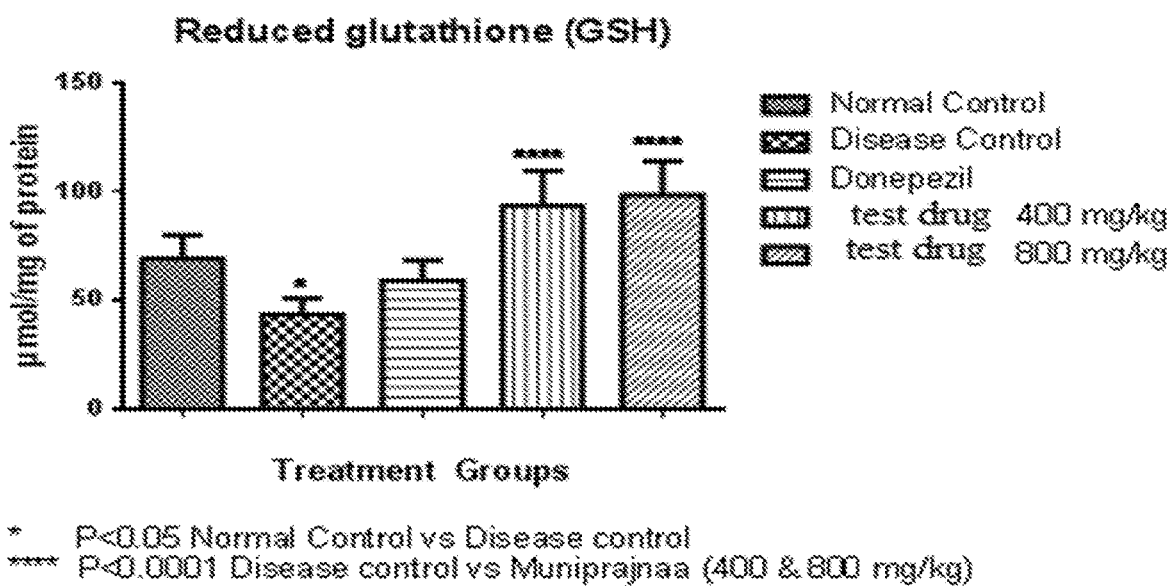
FIG. 7 is a graph depicting the levels of Reduced Glutathione in various treatment groups.

Biochemical parameters: To assess the antioxidant potential of test drug in protecting the mice from memory impairment, we have performed the reduced glutathione (GSH) and lipid peroxidation (LPO) assays. Acetylcholinesterase inhibition activity was also checked by measuring the AChE activity. Test drug at both 400 & 800 mg/kg showed significant ($P<0.0001$) elevation of reduced glutathione levels in comparison to disease control, this is in accordance with the findings from other studies. The standard drug donepezil (5 mg/kg, p.o.) showed an increasing trend in GSH levels but there was no statistical significance observed in comparison to disease control. Whereas, there is no effect observed in any of the groups in lipid peroxidation assay. In the acetylcholinesterase assay, the standard drug and test drug groups have shown a decrease (positive trend) in the AChE levels but, there was no statistical significance observed. Table 16 depicts the results of reduced glutathione (GSH) assay. FIG. 7 is a graph depicting Reduced Glutathione in various treatment groups, wherein Muniprajnaa is the Test drug.

TABLE 16

Reduced glutathione (GSH) assay.
Reduced Glutathione (µmol/mg of protein)

| Treatment | Normal Control | Disease Control | Donepezil (5 mg/kg) | Test drug 400 mg/kg | Test drug 800 mg/kg |
|---|---|---|---|---|---|
| MEAN ± SEM | 69.27 ± 4.82 | 46.63 ± 4.17 | 68.17 ± 9.65 | 94.39 ± 8.96 | 91.26 ± 9.18 |

Figure 8:
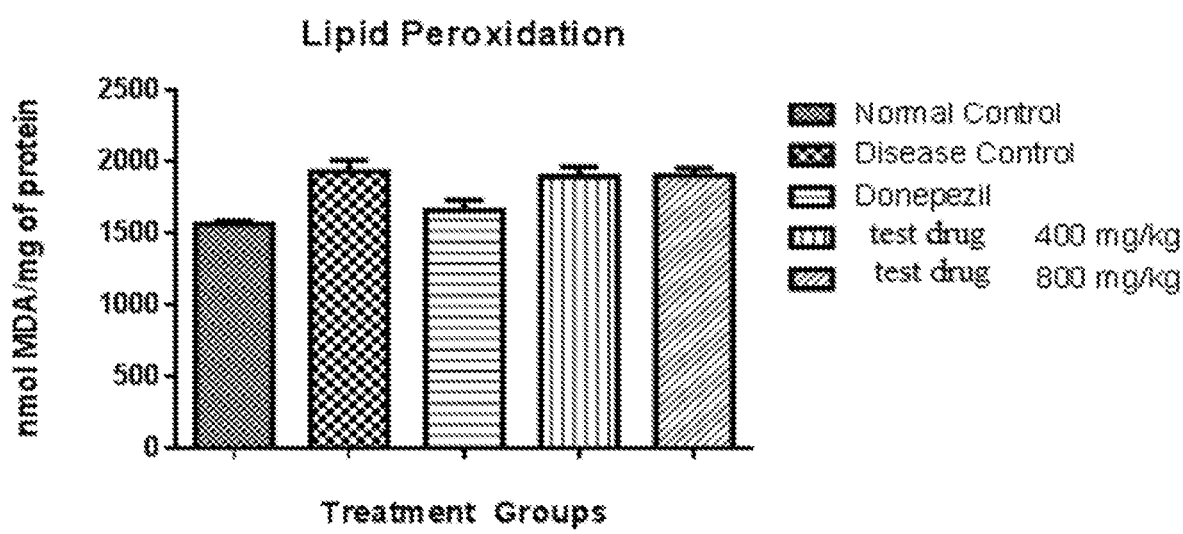
FIG. 8 is a graph depicting results of Lipid peroxidation (LPO) assay in various treatment groups.

Table 17 depicts the results of Lipid peroxidation (LPO) assay. FIG. 8 is a graph depicting Lipid peroxidation (LPO) in various treatment groups, wherein Muniprajnaa is the Test drug.

TABLE 17

Lipid peroxidation (LPO) assay.
Lipid Peroxidation (µmol MDA/mg of protein)

| Treatment | Normal Control | Disease Control | Donepezil (5 mg/kg) | Test drug (400 mg/kg) | Test drug (800 mg/kg) |
|---|---|---|---|---|---|
| MEAN ± SEM | 1752.58 ± 118.4 | 1760.94 ± 121.27 | 1798.77 ± 149.15 | 1860.15 ± 161.54 | 1903.52 + 50.61 |

Values indicated as MEAN ± SEM.

Figure 9:
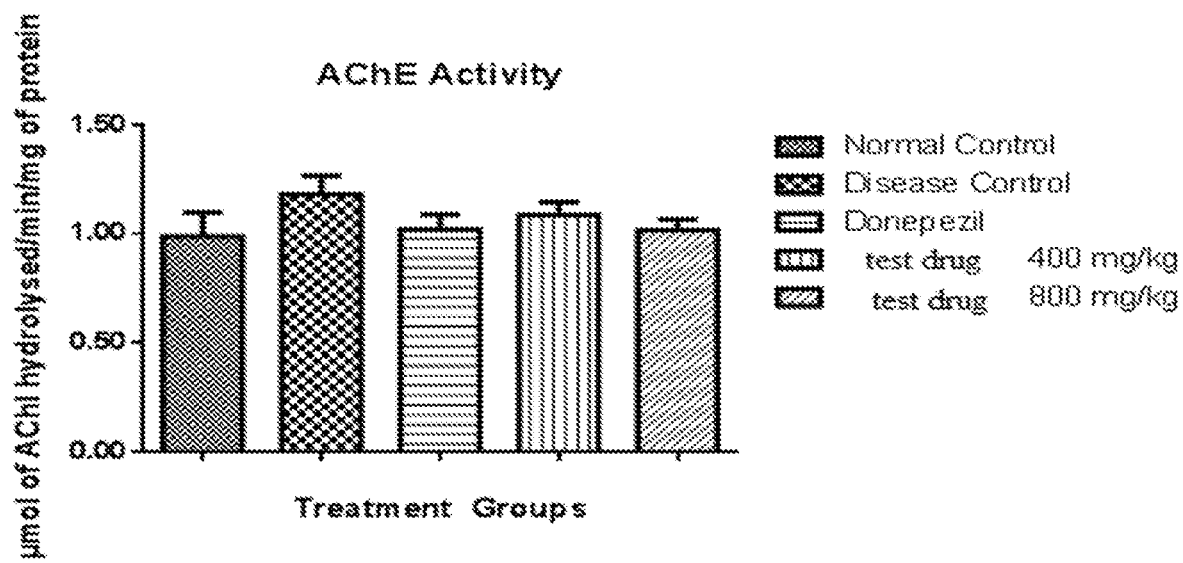
FIG. 9 is a graph depicting Acetyl cholinesterase inhibition activity in various treatment groups, according to embodiments as disclosed herein.

Table 18 depicts the AChE activity. FIG. 9 is a graph depicting AChE activity in various treatment groups, wherein Muniprajnaa is the Test drug.

TABLE 18

AChE activity.
AChE Activity (µmol of AChI hydrolysed/min/mg of protein)

| Treatment | Normal Control | Disease Control | Donepezil (5 mg/kg) | Test drug (400 mg/kg) | Test drug (800 mg/kg) |
|---|---|---|---|---|---|
| Mean ± SEM | 0.987 ± 0.110 | 1.181 ± 0.08 | 1.02 ± 0.06 | 1.085 ± 0.06 | 1.016 ± 0.05 |

Values indicated as MEAN ± SEM.

Discussion and interpretation of results: The present study was aimed to assess the anti-amnesic effect of test drug tablets in acute models of Alzheimer's in mice. The central cholinergic system is important in the regulation of cognitive function. The neurotransmitter acetylcholine (ACh), is required for central and peripheral control of multiple cognitive processes including timing, attention, learning, and memory (Brandon et al., 2004). Therefore, a decrease in ACh results in learning and memory dysfunction. Scopolamine is a nonselective muscarinic ACh receptor (mAChR) antagonist, mainly targets M1 & M2 AChR, thereby impairing learning acquisition and short-term memory in rodents and humans (Dawson, Heyes and Iversen, 1992). In addition, scopolamine is considered to elevate acetyl cholinesterase (AChE) levels in the cortex and hippocampus and has been used to search for and evaluate antidementia drugs. Hence, we have used scopolamine induced memory impairment model. Besides cholinergic hypothesis in learning and memory, many clinical and experimental researches reported that oxidative stress is involved in the pathological characteristics of neurodegenerative disorders including AD (Melo et al., 2011) (Pimentel et al., 2012). Some recent studies have suggested that the dysfunction of learning, memory, and cognition induced by administration of scopolamine in animal models is associated with changes in the expression of antioxidant enzymes (Ahmed and Gilani, 2009). To check this, we have employed the passive avoidance test and the novel object recognition test followed by biochemical assays.

In the present study, attenuation of scopolamine induced memory loss was observed after treatment with Test drug (800 mg/kg, p.o.) both in passive avoidance and novel object recognition tests. The passive avoidance test is used as a useful tool for the estimation of working as well as reference memories. In this model, Test drug (800 mg/kg, p.o.) significantly shortened the time spent in the dark compartment and reduced the number of crossings thereby mitigating the memory deficits produced by scopolamine (1 mg/kg, i.p.). This was comparable to the standard drug donepezil (5 mg/kg, p.o.) which reversed the scopolamine induced memory deficit. In the novel object recognition test, a model which is used for estimation of working memory in animals, scopolamine has significantly impaired the memory and the disease control animals failed to discriminate between the familiar objects and the novel object. Whereas, treatment with Test drug (800 mg/kg, p.o.) has significantly improved the discrimination and recognition index scores.

This is further supported by the positive trend that was observed in the reduced glutathione assay and AChE assay. Particularly in the GSH assay, test drug has significantly elevated the GSH levels and this might be a reason for a positive memory retention effect on the animals suggesting that its effect might be primarily due to antioxidant mechanisms. This is in accordance with research findings by other groups (El-Khadragy, Al-Olayan and Moneim, 2014). In the acetyl cholinesterase assay, there was no statistically significant effect observed on treatment with test drug. Nevertheless, there was a positive trend seen where the standard and test drug treated groups were showing lower activity of acetyl cholinesterase as compared to the disease control groups.

In passive avoidance model, Test drug (800 mg/kg, p.o.) showed a statistically significant (P<0.01) reduction in the time spent by the animals in the dark compartment and increased the number of crossings.

In novel object recognition test model, test drug (800 mg/kg, p.o.) significantly (P<0.05) & (P<0.01) improved the discrimination and recognition indices respectively.

In the biochemical parameters, Test drug at both 400 & 800 mg/kg showed significant (P<0.0001) elevation of reduced glutathione levels in comparison to disease control. And in the acetylcholinesterase assay, the standard drug and test drug groups have shown a decrease (positive trend) in the AChE levels but, there was no statistical significance observed.

As apparent from the results obtained, it is possible that test drug might be acting through the antioxidant mechanisms in mitigating the effect of scopolamine on memory and may provide beneficial effects in treating learning and memory deficits on prolonged treatment at higher dose.

CONCLUSIONS

From the above observations, it can be concluded that test drug tablets have shown a significant effect in preventing the memory impairment effect of scopolamine in both the passive avoidance test and novel object recognition test models. And further the elevation of GSH levels suggests that it might be acting through the antioxidant mechanisms in mitigating the effect of scopolamine on memory. Overall, it suggests that Test drug provides beneficial effects in treating learning and memory deficits on prolonged treatment at higher dose.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

I claim:

1. An oral composition for treatment and management of dementia and cognitive dysfunction, comprising
   therapeutically effective amounts of *Bacopa monnieri* or extracts thereof, *Convolvulus pluricaulis* or extracts thereof, *Mucuna pruriens* or extracts thereof, *Nardostachys jatamansi* or extracts thereof, *Rauwolfia serpentina* or extracts thereof, *Withania somnifera* or extracts thereof, *Acorus calamus* or extracts thereof, *Sida cordifolia* or extracts thereof, *Emblica officinalis* or extracts thereof, Shilajit, Rasa sindura and at least one bhasma, wherein said *Bacopa monnieri* is present in an amount in the range of 4 to 8 wt. % of the total weight of the composition, *Convolvulus pluricaulis* is present in an amount in the range of 2 to 4 wt. % of the total weight of the composition, *Mucuna pruriens* is present in an amount in the range of 2 to 4 wt. % of the total weight of the composition, *Nardostachys jatamansi* is present in an amount in the range of 2 to 4 wt. % of the total weight of the composition, *Rauwolfia serpentina* is present in an amount in the range of 2 to 4 wt. % of the total weight of the composition, *Withania somnifera* is present in an amount in the range of 3 to 7 wt. % of the total weight of the composition, *Acorus calamus* is present in an amount in the range of 2 to 4 wt. % of the total weight of the composition, *Sida cordifolia* is present in an amount in the range of 2 to 4 wt. % of the total weight of the composition, *Emblica officinalis* is present in an amount in the range of 3 to 7 wt. % of the total weight of the composition; and
   at least one ingredient selected from the group consisting of *Santalum album, Pterocarpus santalinus, Glycyrrhiza glabra, Terminalia chebula, Terminalia bellerica, Zingiber officinale, Piper nigrum, Piper longum, Curcuma longa, Inula racemosa, Cinnamomum zeylanica, Elettaria cardamomum, Syzygium aromaticum, Ocimum sanctum, Tinospora cordifolia, Hemidesmus indicus, Vetiveria zizanioides, Alpinia galangal, Cassia fistula, Embelia ribes, Prunus cerasoides, Rubia cordifolia, Ricinus communis, Boerhavia diffusa, Terminalia arjuna, Commiphora mukul, Picrorhiza kurroa, Plumbago zeylanica,* and *Mesua ferrea*, or extracts thereof;
   wherein said composition is in at least one form selected from the group consisting of tablet, pellet, lozenge, granule, suspension and capsule.

2. The composition as claimed in claim 1, wherein said bhasma is selected from the group consisting of Swarna makshika bhasma, Loha Bhasma, Abhraka bhasma, Rajata Bhasma, Muktashukti Bhasma, Pravala Bhasma, Shringa Bhasma, Vanga Bhasma, Yashada Bhasma, Shankha Bhasma and Mandura Bhasma.

3. The composition as claimed in claim 1, wherein said Shilajit is present in an amount of ≤2 wt. % of the total weight of the composition; Rasa sindura is present in an amount of ≤2 wt. % of the total weight of the composition; and at least one bhasma is present in an amount of ≤2 wt. % of the total weight of the composition.

4. The composition as claimed in claim 2, wherein said Swarna makshika bhasma is present in an amount of ≤2 wt. % of the total weight of the composition; Loha Bhasma is present in an amount of ≤2 wt. % of the total weight of the composition; Abhraka bhasma is present in an amount of ≤2 wt. % of the total weight of the composition; Rajata Bhasma is present in an amount of ≤2 wt. % of the total weight of the composition; Muktashukti Bhasma is present in an amount of ≤2 wt. % of the total weight of the composition; Pravala Bhasma is present in an amount of ≤2 wt. % of the total weight of the composition; Shringa Bhasma is present in an amount of ≤2 wt. % of the total weight of the composition; Vanga Bhasma is present in an amount of ≤2 wt. % of the total weight of the composition; Yashada Bhasma is present in an amount of ≤2 wt. % of the total weight of the composition; Shankha Bhasma is present in an amount of ≤2 wt. % of the total weight of the composition; and Mandura Bhasma is present in an amount of ≤2 wt. % of the total weight of the composition.

5. The composition as claimed in claim 1, wherein said *Santalum album* is present in an amount of ≤2 wt % of the total weight of the composition; *Pterocarpus santalinus* is present in an amount of ≤2 wt % of the total weight of the composition; *Glycyrrhiza glabra* is present in an amount of ≤2 wt % of the total weight of the composition; *Terminalia chebula* is present in an amount of ≤2 wt % of the total weight of the composition; *Terminalia bellerica* is present in an amount of ≤2 wt % of the total weight of the composition; *Zingiber officinale* is present in an amount of ≤2 wt % of the total weight of the composition; *Piper nigrum* is present in an amount of ≤2 wt % of the total weight of the composition; *Piper longum* is present in an amount of ≤2 wt % of the total weight of the composition; *Curcuma longa* is present in an amount of ≤2 wt % of the total weight of the composition; *Inula racemosa* is present in an amount of ≤2 wt % of the total weight of the composition; *Cinnamomum zeylanica* is present in an amount of ≤2 wt % of the total weight of the composition; *Elettaria cardamomum* is present in an amount of ≤2 wt % of the total weight of the composition; *Syzygium aromaticum* is present in an amount of ≤2 wt % of the total weight of the composition; *Ocimum sanctum* is present in an amount of ≤2 wt % of the total weight of the composition; *Tinospora cordifolia* is present in an amount in the range of 1 to 3 wt. % of the total weight of the composition; *Hemidesmus indicus* is present in an amount of ≤2 wt % of the total weight of the composition; *Vetiveria zizanioides* is present in an amount of ≤2 wt % of the total weight of the composition; *Alpinia galangal* is present in an amount in the range of 1 to 3 wt. % of the total weight of the composition; *Cassia fistula* is present in an amount in the range of 1 to 3 wt. % of the total weight of the composition; *Embelia ribes* is present in an amount of ≤2 wt % of the total weight of the composition; *Prunus cerasoides* is present in an amount of ≤2 wt % of the total weight of the composition; *Rubia cordifolia* is present in an amount of ≤2 wt % of the total weight of the composition; *Ricinus communis* is present in an amount of ≤2 wt % of the total weight of the composition; *Boerhavia diffusa* is present in an amount of ≤2 wt % of the total weight of the composition; *Terminalia arjuna* is present in an amount of ≤2 wt % of the total weight of the composition; *Commiphora mukul* is present in an amount of ≤2 wt % of the total weight of the composition; *Picrorhiza kurroa* is present in an amount of ≤2 wt % of the total weight of the composition; *Plumbago zeylanica* is present in an amount of ≤2 wt % of the total weight of the composition; and *Mesua ferrea* is present in an amount of ≤2 wt % of the total weight of the composition.

6. The composition as claimed in claim 1, further comprising *Gum acacia*.

7. The composition as claimed in claim 4, wherein *Gum acacia* is present in an amount in the range of 8 to 12 wt. % of the total composition.

8. The composition as claimed in claim 1, said composition comprising *Bacopa monnieri, Convolvulus pluricaulis, Mucuna pruriens, Nardostachys jatamansi, Rauwolfia serpentina, Withania somnifera, Acorus calamus, Sida cordifolia, Emblica officinalis, Santalum album, Pterocarpus santalinus, Glycyrrhiza glabra, Terminalia chebula, Terminalia bellerica, Zingiber officinale, Piper nigrum, Piper longum, Curcuma longa, Inula racemosa, Cinnamomum zeylanica, Elettaria cardamomum, Syzygium aromaticum, Ocimum sanctum, Tinospora cordifolia, Hemidesmus indicus, Vetiveria zizanioides, Alpinia galangal, Cassia fistula, Embelia ribes, Prunus cerasoides, Rubia cordifolia, Ricinus communis, Boerhavia diffusa, Terminalia arjuna, Commiphora mukul, Picrorhiza kurroa, Plumbago zeylanica, Mesua ferrea*, Shilajit, Rasa sindura, Swarna makshika bhasma, Loha Bhasma, Abhraka bhasma, Raj ata Bhasma, Muktashukti Bhasma, Pravala Bhasma, Shringa Bhasma, Vanga Bhasma, Yashada Bhasma, Shankha Bhasma and Mandura Bhasma.

9. A process for the preparation of a composition claimed in claim 1, comprising:
   preparing a grinding decoction comprising *Stereospermum suaveolens* by soaking dry root of *Stereospermum suaveolens* in 16 parts of water and boiling at a temperature in the range of 80° C. to 85° C. for a period until the amount of water is reduced to $\frac{1}{8}^{th}$ of the initial volume;
   levigating at least one bhasma, Rasa sindura, Guggulu and Shilajit with a first portion of said grinding decoction in a grinder; and
   adding powdered herbs comprising whole plant of *Bacopa monnieri* and *Convolvulus pluricaulis*; seeds of *Mucuna pruriens*; rhizome of *Nardostachys jatamansi*; roots of *Rauwolfia serpentina, Withania somnifera, Sida cordifolia* and *Acorus calamus*; and fruits of *Emblica officinalis* into said grinder and grinding with a second portion of said grinding decoction, to obtain a homogenous mass.

10. The process as claimed in claim 9, wherein said powdered herbs further comprises seeds of *Elettaria cardamomum*; roots of *Picrorhiza kurroa, Plumbago zeylanica, Rubia cordifolia, Hemidesmus indicus, Vetiveria zizanioides, Alpinia galangal, Glycyrrhiza glabra* and *Inula racemosa*; fruits of *Terminalia chebula, Terminalia bellerica, Piper nigrum* and *Piper longum*; heartwood of *Santalum album* and *Pterocarpus santalinus*; rhizome of *Zingiber officinale* and *Curcuma longa*; bark of *Cinnamomum zeylanica*; floral bud of *Syzygium aromaticum*; leaves of *Ocimum sanctum*, stem of *Tinospora cordifolia*; bark of *Cassia fistula*; fruit of *Embelia ribes*; heartwood of *Prunus cerasoides*; leaves of *Ricinus communis*; roots of *Boerhavia diffusa*; stem bark of *Terminalia arjuna*; and stamen of *Mesua ferrea*.

11. The process as claimed in claim 9, wherein said bhasma is selected from a group consisting of Swarna makshika bhasma, Loha Bhasma, Abhraka bhasma, Rajata Bhasma, Muktashukti Bhasma, Pravala Bhasma, Shringa Bhasma, Vanga Bhasma, Yashada Bhasma, Shankha Bhasma and Mandura Bhasma.

12. The process as claimed in claim 9, wherein said grinding decoction further comprises *Aloe vera, Centella asiatica, Premna mucronata, Gmelina arborea, Aegle marmelos, Oroxylum indicum, Desmodium gangeticum, Uraria picta, Solanum indicum, Solanum xanthocarpum, Tribulus terrestris, Acorus calamus, Celastrus paniculatus, Nardostachys jatamansi, Rauwolfia serpentina, Alpinia galanga, Asparagus racemosus, Triticum aestivum, Cuminum cyminum, Coriandrum sativum, Apium graveolens, Yavakshara alkali, Sarjikshara alkali* and *Cissus quadrangularis*.

13. The process as claimed in claim 12, wherein preparing said grinding decoction comprises soaking 3 parts of fresh leaves of *Aloe vera*, 3 parts of fresh leaves of *Centella asiatica*, ½ part of dry root of *Stereospermum suaveolens*, ½ part of dry root of *Premna mucronate*, ½ part of dry root of *Gmelina arborea*, ½ part of dry root of *Aegle marmelos*, ½ part of dry root of *Oroxylum indicum*, ½ part of dry plant of *Desmodium gangeticum*, ½ part of dry plant of *Uraria picta*, ½ part of dry root of *Solanum indicum*, ½ part of dry plant of *Solanum xanthocarpum*, ½ part of dry fruit of *Tribulus terrestris*, 2 part of *Acorus calamus*, 2 part of *Celastrus paniculatus*, 2 part of *Nardostachys jatamansi*, 3 part of *Rauwolfia serpentina*, 2 part of *Alpinia galanga*, 1 part fresh roots of *Asparagus racemosus*, 1 part of fresh leves of *Triticum aestivum*, 0.4 part of dry seeds of *Cuminum cyminum*, 0.4 part of dry fruits of *Coriandrum sativum*, 0.4 part of dry seeds of *Apium graveolens*, 0.3 part of *Yavakshara alkali* (Alkali of *Hordeum vulgare*), 0.3 part of *Sarjikshara alkali* (Barilla) and 0.8 part of fresh stem of *Cissus quadrangularis* in 427.2 parts of water; and boiling until the amount of water is reduced to $1/8^{th}$ of the initial volume.

14. The process as claimed in claim 9, further comprising adding *Gum acacia* to said homogenous mass and grinding to obtain a semisolid mass; drying; granulating by wet granulation; and punching to obtain tablets.

15. A method for manufacturing a medicament, comprising combining a suitable excipient and the composition claimed in claim 1.

16. The method as claimed in claim 15, wherein said composition is present in an amount effective for treatment of Dementia.

17. A method for treatment and management of Dementia, said method comprising administering, to a patient in need thereof, a therapeutically effective amount of the composition claimed in claim 1.

18. A method for treatment and management of neurodegenerative disorder, said method comprising administering, to a patient in need thereof, a therapeutically effective amount of the composition claimed in claim 1.

19. A method for improving memory in an individual, said method comprising administering, to said individual, the composition claimed in claim 1.

\* \* \* \* \*